(12) United States Patent
Brown et al.

(10) Patent No.: US 7,976,824 B2
(45) Date of Patent: Jul. 12, 2011

(54) PRODUCTION OF 2-18F-2-DEOXY-D-GLUCOSE VIA SOLID-PHASE SYNTHESIS

(75) Inventors: Lynda Jane Brown, Southampton (GB); Richard Charles Downie Brown, Southampton (GB); Harry John Wadsworth, Amersham (GB); Alexander Jackson, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 1029 days.

(21) Appl. No.: 10/560,553

(22) PCT Filed: Jul. 29, 2004

(86) PCT No.: PCT/GB2004/003287
§ 371 (c)(1), (2), (4) Date: Apr. 18, 2007

(87) PCT Pub. No.: WO2005/012319
PCT Pub. Date: Feb. 10, 2005

(65) Prior Publication Data
US 2007/0274911 A1 Nov. 29, 2007

(30) Foreign Application Priority Data
Jul. 31, 2003 (GB) .................................. 0317920.7

(51) Int. Cl.
A61K 51/00 (2006.01)
A61M 36/14 (2006.01)
C40B 80/00 (2006.01)
C40B 50/18 (2006.01)
B01J 31/00 (2006.01)

(52) U.S. Cl. ...................... 424/1.89; 424/1.11; 424/1.25; 424/1.65; 424/1.73; 506/42; 506/32; 502/159

(58) Field of Classification Search ................. 424/1.11, 424/1.25, 1.65, 1.73, 1.89; 506/42, 32; 502/159
See application file for complete search history.

(56) References Cited

FOREIGN PATENT DOCUMENTS
WO 02/055026 7/2002
WO 03/002157 1/2003

OTHER PUBLICATIONS

Tumelty, et.al., "Traceless Solid-Phase Synthesis of Substituted Benzimidazoles via a Base-Cleavable Linker", Organic Letters, 2001 vol. 3, No. 1 pp. 83-86.
PCT/GB2004/003287 Int'l Search Report dated Oct. 2004.
GB 0317920.7 Search Report dated Jan. 2004.

*Primary Examiner* — Michael G Hartley
*Assistant Examiner* — Leah Schlientz

(57) ABSTRACT

The invention relates to a compound of formula (I): wherein $P^1$, $P^2$, $P^3$, and $P^4$ are each independently hydrogen or a protecting group; and n is an integer of from 2 to 20 and to the use of such compounds for the synthesis of $^{18}$F-FDG.

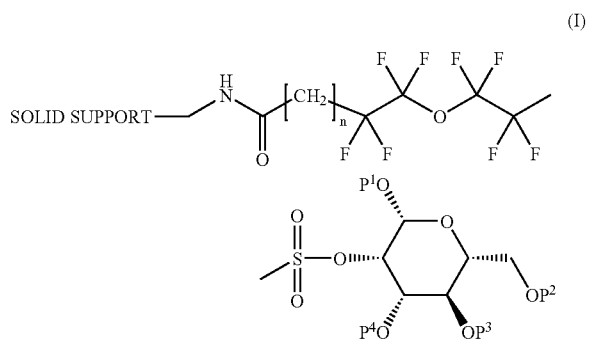

8 Claims, No Drawings

PRODUCTION OF 2-18F-2-DEOXY-D-GLUCOSE VIA SOLID-PHASE SYNTHESIS

This application is a filing under 35 U.S.C. 371 of international application number PCT/GB2004/003287, filed Jul. 29, 2004, which claims priority to application number 0317920.7 filed Jul. 31, 2003, in Great Britain the entire disclosure of which is hereby incorporated by reference.

The present invention relates to novel intermediates for solid-phase production of 2-[$^{18}$F]-fluoro-2-deoxy-D-glucose ($^{18}$F-FDG), a Positron Emission Tomography (PET) radiotracer, and radiofluorination processes using these intermediates. The invention also comprises radiopharmaceutical kits using these novel processes and intermediates.

The favoured radioisotope for PET, $^{18}$F, has a relatively short half-life of 110 minutes. $^{18}$F-labelled tracers for PET therefore have to be synthesised and purified as rapidly as possible, and ideally within one hour of clinical use. Standard synthetic methods for introducing fluorine-18 are relatively slow and require post-reaction purification (for example, by HPLC) which means that it is difficult to obtain the $^{18}$F-labelled tracer for clinical use in good radiochemical yield. There is also a need for automation to protect the operator from radiation exposure. Many radiofluorinations are complicated procedures and it is necessary to simplify them to facilitate automation.

WO 03/002157 describes solid-phase processes for producing $^{18}$F-labelled tracers quickly and with high specific activity yet avoiding time-consuming purification steps, such that the resultant $^{18}$F-labelled tracer is suitable for use in PET. The solid-phase methods also lend themselves to automation with advantages of ease of production and greater throughput. We have now found a particular class of intermediate for production of $^{18}$F-FDG falling within the scope of WO 03/002157, but which have advantages including that they can be synthesised in good yields and which give surprisingly good yields in the radiofluorination reaction.

Thus, according to a first aspect of the invention, there is provided a compound of formula (I):

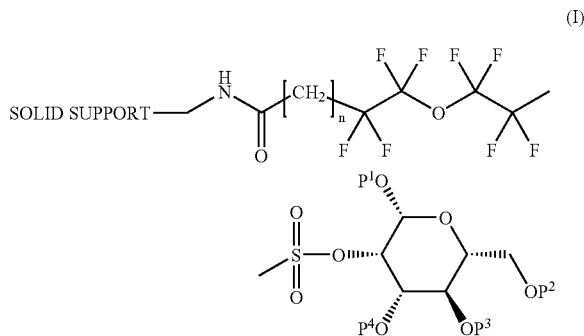

wherein $P^1$, $P^2$, $P^3$, and $P^4$ are each independently hydrogen or a protecting group; and n is an integer of from 2 to 20.

In the compounds of formula (I), n is suitably 4 to 12, preferably 6 to 10, and is most preferably 10.

In the compounds of formula (I), suitable protecting groups, $P^1$, $P^2$, $P^3$, and $P^4$ may be found, for example, in Protecting Groups in Organic Synthesis, Theordora W. Greene and Peter G. M. Wuts, published by John Wiley & Sons Inc. $P^1$ is preferably $C_{1-4}$ alkyl, such as methyl. $P^4$ is preferably $C_{1-4}$ alkoxymethyl, such as ethoxymethyl. $P^2$ and $P^3$, together with the oxygens to which they are attached, suitably form a 1,3-dioxolane, such as a 2-phenyl 1,3-dioxolane (a benzylidene protecting group).

The present invention provides, in a further aspect, a process for the production of 2-$^{18}$F-fluoro-2-deoxy-D-glucose ($^{18}$F-FDG) which comprises treatment of a solid support-bound precursor of formula (I) as defined above, with $^{18}$F$^-$ to produce the labelled tracer of formula (II)

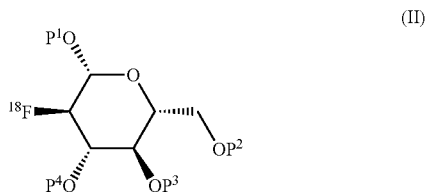

wherein $P^1$, $P^2$, $P^3$, and $P^4$ are each independently hydrogen or a protecting group; optionally followed by
(i) removal of excess $^{18}$F$^-$, for example by ion-exchange chromatography; and/or
(ii) removal of the protecting groups; and/or
(iii) removal of organic solvent; and/or
(iv) formulation of the resultant compound of formula (II) as an aqueous solution.

As the $^{18}$F-labelled tracer of formula (II) is removed from the solid-phase into solution, all unreacted precursor remains bound to the resin and can be separated by simple filtration, thus obviating the need for complicated purification, for example by HPLC. The $^{18}$F-labelled tracer of formula (II) may be cleaned up by removal of excess F$^-$, for example by ion-exchange chromatography and/or by removal of any organic solvent. The resultant $^{18}$F-FDG may then be further made-up into an aqueous formulation for clinical use.

In the compounds of formula (I) the "SOLID SUPPORT" may be any suitable solid-phase support which is insoluble in any solvents to be used in the process but to which the linker can be covalently bound. Examples of suitable SOLID SUPPORT include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel.

Treatment of the compound of formula (I) with $^{18}$F$^-$ may be effected by treatment with any suitable source of $^{18}$F$^-$, such as Na$^{18}$F, K$^{18}$F, Cs$^{18}$F, tetraalkylammonium $^{18}$F fluoride, or tetraalkylphosphonium $^{18}$F fluoride. To increase the reactivity of the fluoride, a phase transfer catalyst such as a crown ether or cryptand for example 4,7,13,16,21,24 hexaoxa-1,10-diazabicyclo[8,8,8] hexacosane may be added and the reaction performed in a non protic solvent. These conditions give reactive fluoride ions. The treatment with $^{18}$F$^-$ is suitably effected in the presence of a suitable organic solvent such as acetonitrile, dimethylformamide, dimethylsulphoxide, tetrahydrofuran, dioxan, 1,2 dimethoxyethane, sulpholane, N-methylpyrolidinineone, at a non-extreme temperature, for example, 15° C. to 180° C., preferably at elevated temperature. On completion of the reaction, the $^{18}$F-labelled tracer of formula (II) dissolved in the solvent is conveniently separated from the solid-phase by filtration.

Any excess $^{18}$F$^-$ may be removed from the solution of $^{18}$F-FDG by any suitable means, for example by ion-exchange chromatography or solid phase absorbents. Suitable ion-exchange resins include BIO-RAD AG 1-X8 or Waters QMA and suitable solid phase absorbents include alumina.

The excess $^{18}F^-$ may be removed using such solid phases at room temperature in aprotic solvents.

Removal of any protecting groups from the compound of formula (II) may be effected by standard methods. Suitable protection and deprotection methodologies may be found, for example, in Protecting Groups in Organic Synthesis, Theodora W. Greene and Peter G. M. Wuts (see above). In a preferred embodiment of the invention, the sugar hydroxyl groups are protected as esters, suitably $C_{1-16}$ alkanoic esters, preferably as acetate esters, or as ethers, preferably $C_{1-6}$ alkoxy methyl ethers, or acetals. Ester, acetal, or ether protecting groups may be conveniently removed by hydrolysis, for example in the presence of acid or base. Such deprotection may be effected on using solid supported acid or base catalysts that render the need for post deprotection neutralisation unnecessary Any organic solvent may be removed by any standard method such as by evaporation at elevated temperature in vacuo or by passing a stream of inert gas such as nitrogen or argon over the solution.

Before use of the $^{18}F$-FDG, it may be appropriate to formulate K, for example as an aqueous solution by dissolving the $^{18}F$-labelled tracer in sterile isotonic saline which may contain up to 10% of a suitable organic solvent such as ethanol, or a suitable buffered solution such as phosphate buffer. Other additives may be added such as ascorbic acid to reduce radiolysis.

Compounds of formula (I) may be prepared by the method shown in Scheme 1 in which n, $P^1$, $P^2$, $P^3$ and $P^4$ are as defined for the compound of formula (I) and p is n−2 wherein n is as defined for the compound of formula (I).

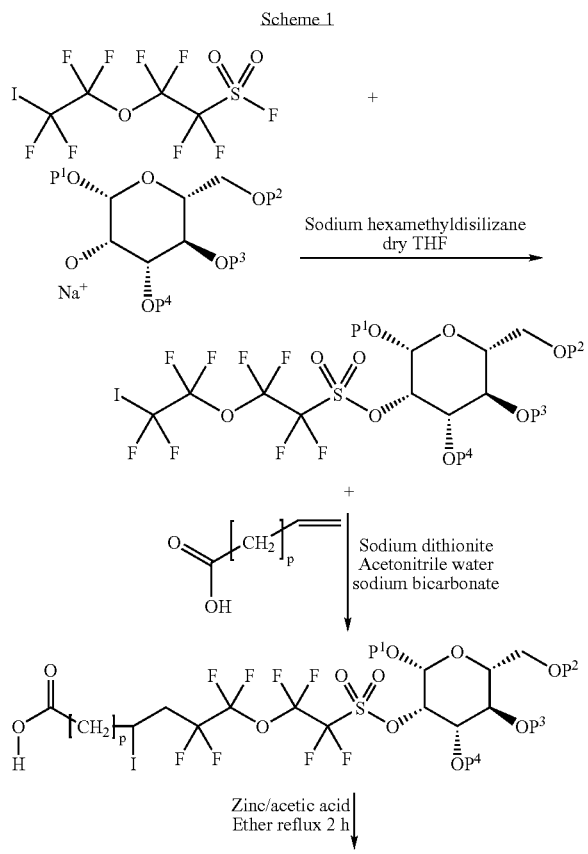

Scheme 1

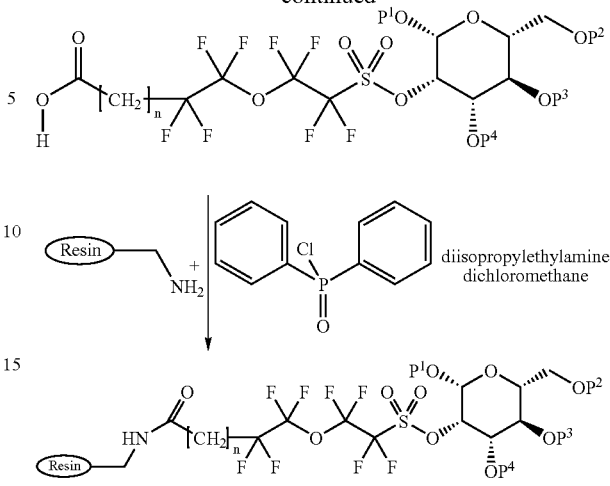

As described above, the advantages of such solid-phase processes for preparation of $^{18}F$-labelled tracers include the relative speed of the process, simplified purification methods and ease of automation—all of which mean that the processes are suitable for preparation of $^{18}F$-labelled tracers for use in PET. Accordingly, the present invention provides the use of a process for the manufacture of $^{18}F$-FDG for use in PET.

Conveniently, the solid support bound precursor of formula (I) could be provided as part of a kit to a radiopharmacy. The kit may contain a cartridge which can be plugged into a suitably adapted automated synthesiser. The cartridge may contain, apart from the solid support-bound precursor, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customers requirements for radioactive concentration, volumes, time of delivery etc.

Conveniently, all components of the kit are disposable to minimise the possibilities of contamination between runs and may be sterile and quality assured.

The invention further provides a radiopharmaceutical kit for the preparation of $^{18}F$-FDG for use in PET, which comprises:
(i) a vessel containing a compound of formula (I); and
(ii) means for eluting the vessel with a source of $^{18}F-$;
(iii) an ion-exchange cartridge for removal of excess $^{18}F-$; and optionally
(iv) a cartridge for solid-phase deprotection of the resultant product of formula (II).

The invention further provides a cartridge for a radiopharmaceutical kit for the preparation of an $^{18}F$-FDG for use in PET which comprises:
(i) a vessel containing a compound of formula (I); and
(ii) means for eluting the vessel with a source of $^{18}F^-$.

In a further aspect of the invention, there is provided a method for obtaining a diagnostic PET image which comprises the step of using a radiopharmaceutical kit or a cartridge for a radiopharmaceutical kit as described above.

The invention will now be illustrated by way of the following Examples. Throughout the Examples, abbreviations used are as follows:

DMF: N,N-dimethylformamide
w/v: weight/volume
h: hour(s)
L: litre(s)
TLC: thin layer chromatography
THF: tetrahydrofuran
eq.: equivalents
DCM: dichloromethane
EtOAc: ethyl acetate
Et$_2$O: diethyl ether
min(s): minute (s)

EXAMPLES

Intermediate 1: Methyl-4,6-O-benzylidine-3-ethoxymethyl-2-(5-Iodooctafluoro-3-oxapentane-sulphonate)-β-D-mannopyranoside Intermediate 1(i)

Synthesis of Methyl 4,6-O-benzylidene-β-D-glucopyranoside

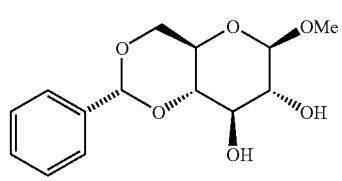

All materials unless specifically referred to were supplied by the Aldrich chemical company.

Using a modification of the procedure as described: Tetrahedron, 1992, 48(47), 10249-10264. Methyl β-D-glucopyranoside (Biosynth International M-3592; 10.2 g, 50 mmol), benzaldehyde dimethylacetal (30 ml, 200 mmol) and 10-camphorsulfonic acid (116 mg, 0.5 mmol) in anhydrous acetonitrile (150 ml) was stirred at room temperature for 4 h. The reaction was checked by TLC to confirm complete conversion to the product (run in hexane: ethyl acetate, 1:2, visualised with ceric ammonium molybdate spray and heating. The reaction was then treated with triethylamine (1 ml) to neutralise the acid. The solution was filtered and the solid was washed with acetonitrile (20 ml). The mother solution was concentrated to about 60 ml, and it was again filtrated, and the filtrate washed with acetonitdrile (10 ml). The combined solid was dried in vacuum, to give 12.9 g (91%) of methyl 4,6-O-benzylidene-β-D-glucopyranoside.

$^1$H NMR (CD$_3$)$_2$SO (300 MHz) TMS ref. δ 3.09(1H, q); 3.42(7H, m); 3.69(1H, t,); 4.18(1H, t,t); 5.35(2H, d,d); 5.57 (1H, s,); 7.37 (3H, m); 7.45 (2H, m).

$^{13}$C NMR (CD$_3$)$_2$SO (300 MHz) TMS ref. δ: 56.4, 65.78, 67.97, 72.81, 74.27, 80.63, 100.67, 104.53, 126.35, 128.03, 128.85, 137.80

Intermediate 1 (ii)

Methyl 4,6-O-benzylidene-3-ethoxymethy-β-D-glucopyranoside

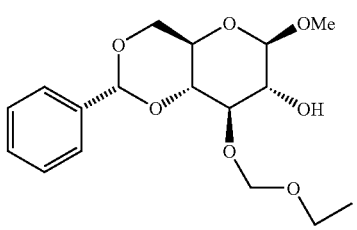

In a 5 L round bottomed flask equipped with an overhead stirrer and held under an atmosphere of nitrogen was placed dry methyl 4,6-O-benzylidene-β-D-glucopyranoside (50 g, 175 mmole) and dry tetrahydrofuran (3.5 L) (Aldrich chromatography grade) and the mixture stirred at room temperature until the sugar had dissolved. Sodium hydride, (16.5 g of a 60% suspension in oil, 0.41 mole, 2.36 eq) was then added with stirring in small portions whilst there was a vigorous evolution of hydrogen over a period of 15 min. When the sodium hydride is added to the methyl 4,6-O-benzylidene-β-D-glucopyranoside, effervescence is vigorous. It should therefore be added in smaller portions to ensure that the effervescence does not exceed the capacity of the flask. Only a minor exotherm was observed (~3° C.). The reaction became quite viscous at this point.

Ethoxy methyl chloride (20 g, 19.3 ml, 0.2127 mole, 1.21 eq) was dissolved in dry THF (100 ml) and added via a dropping funnel to the reaction mixture over a period of 15 min and stirring was continued for 20 h at room temperature. The reaction was then monitored by TLC ethyl acetate; visualised with ceric ammonium molybdate spray, appendix (a). The TLC gave 4 spots.

| | |
|---|---|
| 2,3-Dialkylated sugar | RF 0.78 |
| 2-alkylated product | RF 0.52 |
| 3-alkylated product | RF 0.26 |
| Starting material | RF 0.04 |

The amount of starting material had been reduced almost to nothing after 20 h and the reaction was worked up. The reaction was cautiously quenched by the dropwise addition of water (10 ml) to destroy any excess sodium hydride and the resulting solution concentrated in vacuum (to 250 ml) partitioned between aqueous saturated sodium hydrogen carbonate (500 ml) and ethyl acetate (1 L). The upper ethyl acetate layer was separated and dried over sodium sulphate. The aqueous layer was extracted with a further 2×500 ml of ethyl acetate and the combined ethyl acetate solutions concentrated in vacuum to give a yellow oil (95 g).

The product was divided into two and chromatographed in two portions on flash silica (BDH Silica gel for flash chromatography Product 153325 d10-33 um, d90-70 um) (silica gel dimensions 75 mm×300 mm, column 75 mm diameter 400 mm) in a gradient of 40-60 petroleum ether: ethyl acetate. The crude product was dissolved in 2:1 40-60 petroleum ether:

ethyl acetate in order to load it onto the flash column. If the reaction is nearly complete all the crude material goes into solution, as only the starting methyl 4,6-O-benzylidene-β-D-glucopyranoside is relatively insoluble in this solvent. The column was eluted sequentially with 2.5 L; 2:1 40-60 petroleum ether: ethyl acetate; 2 L of 1.5:1 40-60 petroleum ether: ethyl acetate and 2.5 L 1:1 40-60 petroleum ether:ethyl acetate. 40 ml Fractions were collected, monitored by TLC 1:1 40-60 petroleum ether: ethyl acetate) and visualised with ceric ammonium molybdate spray, appendix (a). The TLC indicated 4 main products.

The four products were concentrated in vacuum to give:
Fastest running compound: Fractions 24-33. Mineral oil
Product 3a: Fractions 40-62. Methyl 4,6-O-benzylidine-2,3-diethoxymethyl-β-D-glucopyranoside Mwt=398 Wt 7.689 g 0.0193 moles yield 11.0%
Product 3b: Fractions 73-91. Methyl 4,6-O-benzylidine-2-ethoxymethyl-β-D-glucopyranoside Mwt=340 Wt 8.73 g 0.0256 moles yield 14.6%
Product 3: Fractions 95-150. Methyl 4,6-O-benzylidine-3-ethoxymethyl-β-D-glucopyranoside Mwt=340 Wt 32.603 g 0.0958 moles yield 54.8%
$^1$H NMR CDCl$_3$ (300 MHz) δ 1.25(3H, s), 3.34(1H,t), 3.43 (1H, m), 3.58(5H, m), 3.75(4H, M), 3.92(1H, m), 4.33(2H, d, d), 4.73(1H,d), 4.80(1H, q), 5.53(1H, q), 7.35(3H, m), 7.48 (2H, m).

Representing 80% recovery of product.

Intermediate 1 (iii)

Methyl 4,6-O-benzylidene-3-O-ethoxymethyl-2-keto-β-D-glucopyranoside

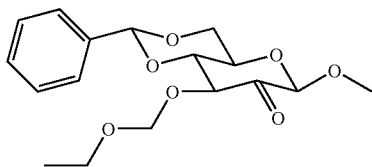

Methyl 4,6-O-benzylidene-3-ethoxymethyl-β-D-glucopyranoside (prepared as described in Intermediate 1(ii)) (14 g, 41.2 mmoles) was treated with methylsulfoxide (168 ml) and acetic anhydride (84.5 ml) at room temperature for 24 h. Thin layer chromatography (40-60 hexanes)/Ethyl acetate 1:1 or 100% diethylether) developed with cerium ammonium molybdate and heating (see procedure above) indicated complete conversion to the ketone. The solution was then diluted with ethyl acetate (1 L) and washed with thorough shaking in a separating funnel with saturated aqueous potassium carbonate solution (600 ml) to hydrolyze the excess acetic anhydride. Caution: Excess potassium carbonate solution must be used as unreacted acetic anhydride can hydrolyze in the water to give acetic acid, which deprotects the sugar. In addition, with insufficient base large amounts of carbon dioxide are liberated causing frothing. The ethyl acetate layer was separated and washed with water (3×500 ml) which was sequentially back extracted with ethyl acetate (3×500 ml). The ethyl acetate fractions was dried over sodium sulphate and concentrated in vacuum to give a semi crystalline solid, crude methyl 4,6-O-benzylidine-3-ethoxymethyl-2 keto-β-D-glucopyranoside. (~20 g >100% containing ethyl acetate) A sample was crystallised from diethyl ether/petrol ether. From the NMR the compound is mixture of the ketone and water in the solvent, in equilibrium with the diol.

$^1$H NMR CDCl$_3$ (300 MHz) δ; 1.09 and 1.16 (3H, t,); 1.65(1H, s); 2.61(1H, s); 3.45(1H, m,); 4.5 (1H, S,); 4.8 (1H, d); 4.87 (1H, d); 4.95(1H, d,); 5.38 (1H, s); 5.54 (1H, s,); 7.4 (3H, m,); 7.49(2H, m,);

$^{13}$C NMR CDCl$_3$ (75 MHz) δ; 14.79, 40.97, 57.19, 57.84, 63.77, 64.37, 64.59, 66.57, 68.55, 78.54, 81.84, 82.94, 92.55, 92.89, 94.9, 101.25, 101.62, 102.93, 126.19, 128.25, 129.11, 136.76, 1327.17.

The crude material contains methyl-2-acetoxy-4,6-O-benzylidine-3-ethoxymethyl-β-D-glucopyranoside from acetylation of the starting material rather than oxidation. This crude material was used directly in the next step.

Intermediate 1.(iv)

Preparation of Methyl 4,6-O-benzylidene-3-ethoxymethyl-β-D-mannopyranoside

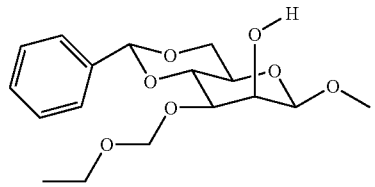

Methyl 4,6-O-benzylidene-3-ethoxymethyl-2-keto-β-D-glucopyranoside (~20 g of crude material from the previous step, 0.0412 Mole assuming 100% yield) in methanol (200 ml) was treated with sodium borohydride (1.686 g, 0.444 mmole) at —20° C. with continuous stirring and allowed to warm to room temperature over 48 h. The reaction was then monitored by TLC (100% diethyl ether) visualised with ceric ammonium molybdate and heating, appendix (a). The ketone has almost the same Rf as the alcohol as it exists as a diol. The reaction was then concentrated in vacuum to a gum and the product partitioned between ethyl acetate (250 ml) and dilute aqueous potassium carbonate solution (50 ml). The ethyl acetate layer was separated and dried over sodium sulfate. The aqueous layer was reextracted with ethyl acetate (2×100 ml), dried over the sodium sulphate and the combined ethyl acetate extracts evaporated to give an off white solid. This material was chromatographed on flash silica (BDH Silica gel for flash chromatography Product 153325 d10-33 um, d90-70 um) (silica gel dimensions 75 mm×200 mm, column 75 mm diameter 400 mm) in a gradient of 40-60 petroleum ether: ethyl acetate. The column was eluted sequentially with 2.L; 1:1 40-60 petroleum ether: ethyl acetate; 2L of 1:1.5 40-60 petroleum ether:ethyl acetate and 2.5 L ethyl acetate. 40 ml Fractions were collected, monitored by TLC (1:1 40-60 petroleum ether: ethyl acetate) and visualised with ceric ammonium molybdate spray ( ) The TLC indicated 3 main products.

The three products were concentrated in vacuum to give:
Product 1: Fractions 10-30. Methyl 2-acetoxy4,6-O-benzylidene-3-ethoxymethyl-β-D-glucopyranoside (1.54 g 0.0040 mole), 9.8%
Product 2: Fractions 35-48. Methyl 4,6-O-benzylidene-3-ethoxymethyl-β-D-glucopyranoside (2.743 g, 0.00806 mole), 19.58% Very crude did not crystallise. Probably only 50% compound.

Product 3: Fractions 50-73. Methyl 4,6-O-benzylidene-3-ethoxymethyl-β-D-mannopyranoside (10.62 g, 0.0312 mole), 76% over two steps. Crystallisation from ether gave 7.84 g of very pure material and 2.78 g of solid on evaporation of the mother liquors, which was suitable for use in the next step.

Together representing 105% recovery of product probably reflecting contamination of fraction 2 with dimethylsulphoxide.

$^1$H NMR CDCl$_3$ (300 MHz) δ: 1.19 (3H, t,) 1.60(1H, s), 2.54(1H, s); 3.39(1H, m,); 3,59(3H, s,); 3.64(2H, m,) 3.77 (2H, m,); 4.09 (1H, t), 4.37(1H, d, d); 4.51 (1H,s,); 4.78 (1H, d,) 4.85, 1H, d,); 5.54(1H, s,); 7.36 (3H, m,) 7.47 (2H, m).

$^{13}$C NMR CDCl$_3$ (75 MHz) δ; 14.8, 57.10, 63.41, 66.81, 68.40, 70.07, 74.57, 77.42, 94.51, 101.51, 126.29, 128.54, 128.78, 137.21.

Intermediate 1 (v)

Methyl-4,6-O-benzylidine-3-ethoxymethyl-2-(5-Iodooctafluoro-3-oxapentanesulphonate)-β-D-mannopyranoside

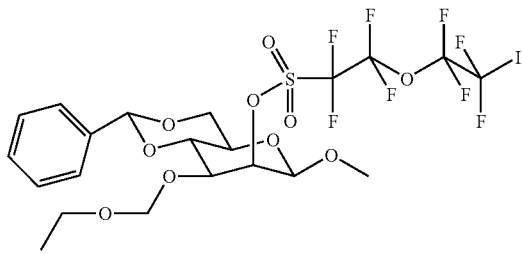

Methyl 4,6-O-benzylidine-3-ethoxymethyl-β-D-manopyranoside (Intermediate 1(iv)) (1 g, 2.93 mMole) was dissolved in dry THF (30 ml) under dry nitrogen and treated with 1 molar sodium hexamethyldisilizane in THF (4.43 ml, 4.43 mmole, 1.5 eq) and stirred for 5 minutes, and then treated with 5-iodooctafluoro-3-oxapentafluorosulphonyl fluoride (Appollo, 1.89 g, 4.43 mmole). The reaction was stirred at room temperature for 1 h. The reaction was monitored by TLC on silica developed in ethyl acetate and visualised by spraying with cerium ammonium molybdate and heating.

The reaction was concentrated in vacuum to low volume, (to remove the excess 5-Iodooctafluoro-3-oxapentafluoro sulphonyl fluoride and the tetrahydrofuran) diluted with ethyl acetate (30 ml) and washed with saturated aqueous sodium hydrogen carbonate solution. The organic phase was separated and dried over sodium sulphate and concentrated in vacuum to a gum. The aqueous phase was reextracted with ethyl acetate (2×30 ml), the extracts dried over sodium sulphate and the combined ethyl acetate extracts concentrated in vacuum to give Methyl-4,6-O-benzylidine-3-ethoxymethyl-2-(5-Iodooctafluoro-3-oxapentanesulphonate)-β-D-mannopyranoside(2.712 g).

$^1$H NMR CDCl$_3$ (300 MHz) TMS ref. δ 7.50-7.30 (5H, m, Ph), 5.57 (1H, s, PhCHO$_2$), 5.13 (1H, d, J=2.9 Hz, H$^2$), 4.81 (2H, AB, J=7.4, 21.3 Hz, OCH$_2$O) 4.57 (1H, s, H$^1$), 4.34 (1H, dd, J=5.1, 10.3 Hz, H$^6$), 4.12 (1H, dd, J=2.9, 9.6 Hz, H$^3$), 3.94-3.82 (2H, m, H$^4$, H$^6$), 3.74-3.55 (2H, m, CH$_2$), 3.56 (3H, s, CH$_3$O), 3.44 (1H, ddd, J=4.4, 9.5, 10.3 Hz, H$^5$), 1.13 (3H, t, J=6.6 Hz, CH$_3$);

$^{13}$C NMR CDCl$_3$(75 MHz,) TMS ref. δ: 137.13, 129.28, 128.37, 126.19, 101.92 (PhCHO$_2$), 99.16 (C$^1$), 94.07 (OCH$_2$O), 83.61 (C$^2$), 77.32 (C$^4$), 71.04 (C$^3$), 68.44 (C$^6$), 67.58 (C$^5$), 63.96 (CH$_2$O), 57.50 (CH$_3$O), 15.01 (CH$_3$);

$^{19}$F NMR CDCl$_3$ (282 MHz) ref. C$_6$F$_6$ δ: 96.98, 79.97, 76.42, 48.24.

$v_{max}$(film)/cm$^{-1}$ 2973 w, 2941 w, 1738 m, 1413 m, 1380 m, 1337 m, 1295 m, 1209 s, 1148 s, 1094 s, 1026 s, 917 m;

Example 1

Preparation of Methyl-4,6-O-benzylidine-3-ethoxymethyl-2-(3-oxa-12,12,13,13,15,15,16,16-Octafluoro-hexadecanioc acid-16-sulphonate)-β-D-mannopyranoside amino polystyrene resin amide Example 1 (i)

Methyl-4,6-O-benzylidine-3-ethoxymethyl-2-(3-oxa-12,12,13,13,15,15,16,16-Octafluoro-10-iodo-hexadecanioc acid-16-sulphonate)-β-D-mannopyranoside

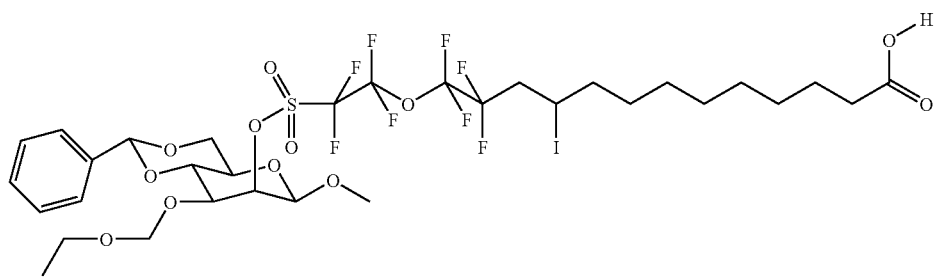

Methyl-4,6-O-benzylidine-3-ethoxymethyl-2-(5-Iodooctafluoro-3-oxapentane sulphonate-β-D-mannopyranoside (crude Intermediate 1) (2.7 g 2.96 mmole theoretical) was dissolved in acetonitrile (40 ml) water (20 ml) cooled to 0° C. on an ice bath, stirred and treated with sodium hydrogen carbonate (298 mg, 3.55 mmole 1.2 eq) sodium dithionite (617 mg, 3.55 mmole, 1.2 eq) and undecylenic acid (Aldrich, 544 mg, 2.96 mmole, 1.0 eq). The stirred reaction was allowed to warm to room temperature over 1 h. The reaction was monitored by TLC on silica developed in ethyl acetate and visualised by spraying with cerium ammonium molybdate and heating.

The reaction was concentrated at room temperature in high vacuum to 20 ml to remove the acetonitrile, and extracted with ethyl acetate (30 ml). (The separation of the two layers is rather slow). The ethyl acetate layer was separated and washed with water (30 ml). The aqueous extracts were sequentially reextracted with ethyl acetate (3×30 ml) and the combined ethyl acetate extracts were dried over sodium sulphate and concentrated in high vacuum at room temperature to a gum to give Methyl-4,6-O-benzylidine-3-ethoxymethyl-2-(3-oxa-12,12,13,13,15,15,16,16-octafluoro-10-iodo-hexadecanioc acid-16-sulphonate)-β-D-mannopyranoside (3.1 g). The crude material was used directly in the next step without further purification. The material was stored at −25° C. overnight to ensure that it did not decompose. A sample of the compound was purified by chromatography on silica in a gradient of ethyl acetate in petrol to give a pure sample.

$^1$H NMR CDCl$_3$ (300 MHz) TMS ref. δ: 7.50-7.31 (5H, m, Ph), 5.58 (1H, s, PhCHO$_2$), 5.15 (1H, d, J=2.9 Hz, H$^2$), 4.80 (2H, AB, J=7.4 Hz, OCH$_2$O), 4.61 (1H, s, H$^1$), 4.40-4.25 (1H, m, CHI, H$^6$), 4.17 (1H, dd, J=2.9, 10.3 Hz, H$^3$), 3.95-3.85 (2H, m, H$^4$, H$^6$), 3.75-3.60 (2H, m, CH$_2$), 3.58 (3H, s, CH$_3$O), 3.51-3.42 (1H, m, H$^5$), 3.00-2.65 (2H, m, CH$_2$), 2.35 (2H, t, J=7.4 Hz, CH$_2$), 1.90-1.30 (14H, m, CH$_2$), 1.15 (3H, t, J=6.6 Hz, CH$_3$);

$^{13}$C NMR CDCl$_3$ (75 MHz) δ: 179.52 (CO), 137.31, 129.51, 128.41, 126.35 (Ph), 102.09 (PhCHO$_2$), 99.37 (C$^1$), 94.15 (OCH$_2$O), 83.73 (C$^2$), 77.48 (C$^4$), 71.28 (C$^3$), 68.60 (C$^6$), 67.79 (C$^5$), 64.14 (CH$_2$O), 57.62 (CH$_3$O), 41.54, 40.58, 34.19, 29.74, 29.41, 29.38, 29.26, 28.71, 24.93 (CH$_2$), 21.36 (CHI), 15.12 (CH$_3$);

$^{19}$F NMR CDCl$_3$ (282 MHz), ref. C$_6$F$_6$ δ: 79.78, 74.37, 47.92, and 43.70.

m/z (ES$^-$) 929.3 [M]$^-$.

ν$_{max}$ (film)/cm$^{-1}$ 2972 w, 2931 w, 2858 w, 1709 m, 1410 m, 1192 s, 1147 s, 1093 s, 1025 s, 993 s, 919 s;

Example 1(ii)

Methyl-4,6-O-benzylidine-3-ethoxymethyl-2-(3-oxa-12,12,13,13,15,15,16,16-Octafluoro-hexadecanioc acid-16-sulphonate)-β-D-mannopyranoside

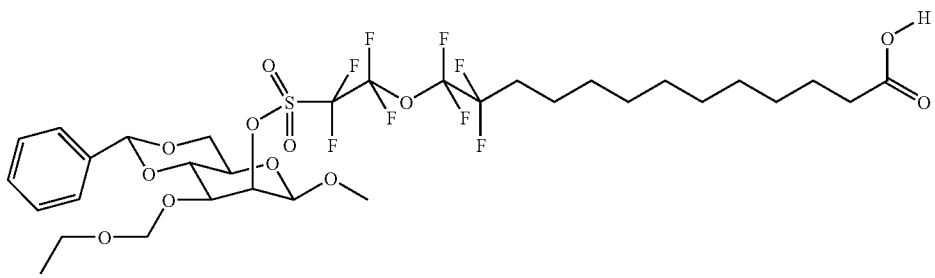

Methyl-4,6-O-benzylidine-3-ethoxymethyl-2-(3oxa -12,12,13,13,15,15,16,16-Octafluoro-10-iodo-hexadecanioc acid-16-sulphonate)-β-D-mannopyranoside (prepared as described in Example 1(i))(2.96 mmol, 2.75 g) was dissolved in dry diethyl ether (40 ml) and dry acetic acid (20 ml) and treated with zinc powder (1150 mg, 17.8 mmoles, 6 eq) under an atmosphere of nitrogen. The reaction was stirred at reflux temperature on an oil bath at 70° C. for 2.5 h. Internal temperature measured to be 45-50° C. TLC of the reaction run in ethyl acetate and developed with cerium ammonium molybdate and heating showed no change in the RF of the main spot.

The reaction was then cooled to room temperature, decanted from the unreacted zinc powder. The zinc powder was washed with ether and the combined solution of acetic acid and diethyl ether concentrated in high vacuum on a rotary evaporator. The gummy residue on evaporation was dissolved in ethyl acetate (50 ml) and washed with water (50 ml). The water layer was reextracted with ethyl acetate (2×25 ml) and the combined organic extracts were separated, dried over sodium sulphate and concentrated in vacuum to give the desired product as a gum. 2.4 g Crude product which was used directly in the next step Before storage the gum was azeotroped with toluene (3×30 ml) under high vacuum at room temperature to remove all traces of acetic acid and water. A sample of The crude product was purified by flash column chromatography on silca gel (3 cm diameter column, 20 cm silica depth, eluting with 2:1 petrol:ethyl acetate to 1:1, the desired product having an Rf=0.6 in neat ethyl acetate) giving a colourless oil (1.05 g, 55% for two steps). The oil was placed under high vacuum for 24 hours to remove trace solvents.

$^1$H NMR CDCl$_3$ (300 MHz) TMS ref. δ, 7.50-7.31 (5H, m, Ph), 5.58 (1H, s, PhCHO$_2$), 5.15 (1H, d, J=2.9 Hz H$^2$), 4.80 (2H, AB, J=7.4 Hz, OCH$_2$O), 4.61 (1H, s, H$^1$), 4.40-4.25 (1H, m, CHI, H$^6$), 4.17 (1H, dd, J=2.9, 10.3 Hz, H$^3$), 3.95-3.85 (2H, m, H$^4$, H$^6$), 3.75-3.60 (2H, m, CH$_2$), 3.58 (3H, s, CH$_3$O), 3.51-3.42 (1H, m, H$^5$), 3.00-2.65 (2H, m, CH$_2$), 2.35 (2H, t, J=7.4 Hz, CH$_2$), 1.90-1.30 (14H, m, CH$_2$), 1.15 (3H, t, J=6.6 Hz, CH$_3$), $^{13}$C NMR CDCl$_3$ (75 MHz) δ: 179.64 (CO), 137.31, 129.39, 128.48, 126.34 (Ph), 102.08 (PhCHO$_2$), 99.38 (C$^1$), 94.14 (OCH$_2$O), 83.57 (C$^2$), 77.46 (C$^4$), 71.31 (C$^3$), 68.59

($C^6$), 67.78 ($C^5$), 64.11 ($CH_2O$), 57.58 ($CH_3O$), 34.22, 30.89, 30.67, 30.45, 29.57, 29.45, 29.36, 29.30, 24.95, 20.56 ($CH_2$), 15.09 ($CH_3$);

$^{19}F$ NMR $CDCl_3$, (282 MHz) ref. $C_6F_6$ δ: 79.8, 74.2, 47.9, and 43.5. m/z ($ES^-$) 803.3 $[M]^-$.

$v_{max}$ (film)/$cm^{-1}$ 2929w, 2858w, 2858w, 1710m, 1411m, 1147s, 1093s, 1025s, 994s, 918s;

Crude Methyl-4,6-O-benzylidine-3-ethoxymethyl-2-(3-oxa-12,12,13,13,15,15,16,16-Octafluoro-hexadecanioc acid-16-sulphonate)-β-D-mannopyranoside from Example 1(ii) was dried by azeotroping with toluene (10 ml) three times (804 mg, 1 mmole) in dry dichloromethane (7.5 ml) in a Coming 20 ml centrifuge tube was treated with Aminopolystryene resin (Nova biochem 01-64-0143 1.4 mmole/g, lot A24595, 500 mg, 0.7 mmole), Diisopropylethylamine (260 mg, 2 mmole) and diphenylphosphoryl chloride (236 mg, 1 mmole). The reaction was shaken on a blood wheel at room temperature for 15 h.

The resin was then collected by filtration and washed sequentially with dichloromethane (100 ml) and methanol (100 ml) and ether (50 ml). The resin was dried in high vacuum to constant weight to give 973 mg of Methyl-4,6-O-benzylidine-3-ethoxymethyl-2-(3-oxa-12,12,13,13,15,15,16,16-Octafluoro-hexadecanioc acid-16-sulphonate)-β-D-mannopyranosideAmino polystyrene Resin amide.

Gel phase NMR run by preparing a slurry of the resin in $CDCl_3$ and running as normal.

$F^{19}$ NMR $CDCl_3$ $CFCl_3$ ref δ: 82.4, 88.5, 114.2, 118.58.

Example 2

Preparation of Methyl-4,6-O-benzylidene-3-ethoxymethyl-2-(8-oxa-6,6,7,7,9,9,10,10-Octafluoro-decanioc acid-10-sulphonate)-β-D-mannopyranoside Amino polystyrene Resin amide

Example 1(iii)

Methyl-4,6-O-benzylidine-3-ethoxymethyl-2-(3-oxa-12,12,13,13,15,15,16,16-Octafluoro-hexadecanioc acid-16-sulphonate)-β-D-mannopyranoside amino polystyrene resin amide

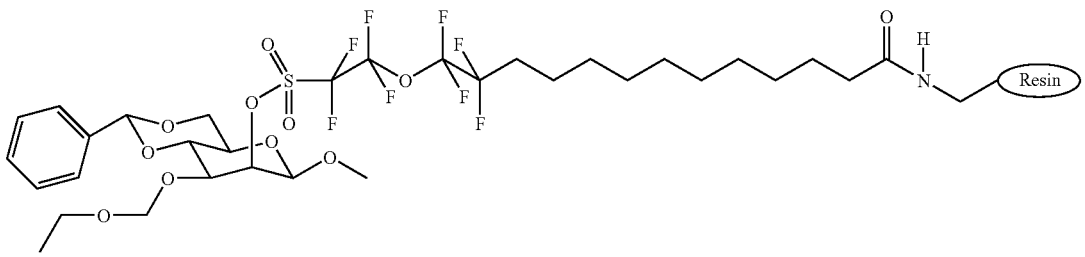

Example 2(i)

Preparation of Methyl-4,6-O-benzylidene-3-ethoxymethyl-2-(4-iodo 8-oxa-6,6,7,7,9,9,10,10-Octafluoro-decanioc acid-10-sulphonate)-β-D-mannopyranoside

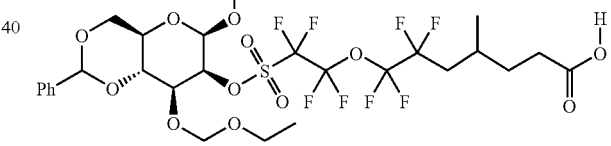

To Methyl-4,6-O-benzylidine-3-ethoxymethyl-2-(5-lodooctafluoro-3-oxapentane sulphonate)-β-D-mannopyranoside (Intermediate 1) (400 mg, 0.54 mmol) and 4-pentenoic acid (56 mg, 0.56 mmol) in $CH_3CN:H_2O$ (4 mL:2 mL) was added $NaHCO_3$ (59 mg, 0.70 mol) and $Na_2S_2O_4$ (85%, 140

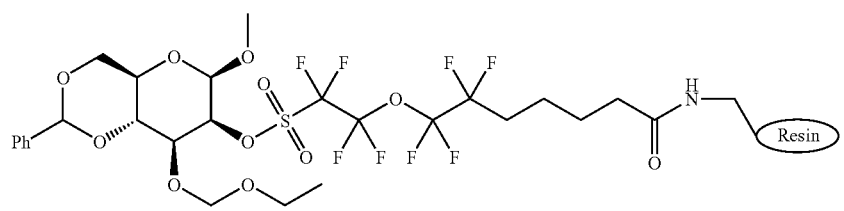

mg, 0.70 mmol) and the reaction stirred at room temperature for 20 mins. The reaction was concentrated in vacuo. Purification by silica gel column chromatography eluting with EtOAc: hexane (1:2) afforded Methyl-4,6-O-benzylidene-3-ethoxymethyl-2-(4-iodo 8-oxa-6,6,7,7,9,9,10,10-Octafluoro-decanioc acid-10-sulphonate)-β-D-mannopyranoside as a colourless oil 305 mg, 67%).

$^1$H NMR (300 MHz, CDCl$_3$) δ: 7.50-7.25 (5H, m, Ph), 5.52 (1H, s, PhCHO$_2$), 5.17 (1H, d, J=2.9 Hz, H$^2$), 4.75 (2H, AB, J=7.4 Hz, OCH$_2$O), 4.53 (1H, s, H$^1$), 4.34-4.24 (2H, m, H$^6$, CHI), 4.09 (1H, dd, J=2.9 Hz, H$^3$), 3.90-3.77 (2H, m, H$^4$, H$^6$), 3.70-3.50 (2H, m, CH$_2$), 3.50 (3H, s, CH$_3$O), 3.45-3.32 (1H, m, H$^5$), 2.98-2.28 (4H, m, CH$_2$), 2.18-1.90 (2H, m, CH$_2$), 1.05 (3H, t, J=7.4 Hz, CH$_3$);

$^{13}$C NMR (75 MHz, CDCl$_3$) δ: 177.32, 137.12, 129.28, 128.36, 126.20 (Ph), 101.93 (PhCHO$_2$), 99.19 (C$^1$), 94.02 (OCH$_2$O), 83.66 (C$^2$), 77.28 (C$^4$), 71.10 (C$^3$), 68.43 (C6), 67.61 (C$^5$), 64.01 (CH$_2$O), 57.54 (CH$_3$O), 41.37, 35.14, 34.21, 19.09 (CH$_2$), 14.98 (CH$_3$); $^{19}$F NMR (282 MHz, CDCl$_3$, ref. C$_6$F$_6$) δ: 79.74, 72.97, 47.56, 43.89; m/z (ES$^+$) 740.9 [M+Na]$^+$, 1458.4 [2M+Na]$^+$.

$v_{max}$ (film)/cm$^{-1}$ 2975w, 2878w, 1714m, 1410m, 1192s, 1146s, 1093s, 1025s, 994m, 920s;

chromatography, eluting with EtOAc: hexane (1:3), afforded Methyl-4,6-O-benzylidene-3-ethoxymethyl-2-(8-oxa-6,6,7,7,9,9,10,10-Octafluoro-decanoic acid-10-sulphonate)-β-D-mannopyranoside as a colourless oil (70 mg, 27%).

$^1$H NMR (300 MHz, CDCl$_3$) δ: 7.50-7.31 (5H, m, Ph), 5.58 (1H, s, PhCHO$_2$), 5.15 (1H, d, J=2.9 Hz, H$^2$), 4.80 (2H, AB, J=7.4 Hz, OCH$_2$O), 4.63 (1H, s, H$^1$), 4.36 (1H, q, J=5.2 Hz, H$^6$), 4.17 (1H, dd, J=2.9, 10.3 Hz, H$^3$), 3.95-3.86 (2H, m, H$^4$, H$^6$), 3.75-3.60 (2H, m, CH$_2$), 3.58 (3H, s, CH$_3$O), 3.52-3.43 (1H, m, H$^5$), 2.42 (2H, t, J=7.4 Hz, CH$_2$), 2.20-2.00 (2H, m, CH$_2$), 1.80-1.60 (4H, m, CH$_2$), 1.15 (3H, t, J=7.4 Hz, CH$_3$);

$^{13}$C NMR (75 MHz, CDCl$_3$) δ: 178.65 (CO), 137.11, 129.29, 128.37, 126.20 (Ph), 101.92 (PhCHO$_2$), 99.19 (C$^1$), 93.99 (OCH$_2$O), 83.50 (C$^2$), 77.27 (C$^4$), 71.08 (C$^3$), 68.42 (C$^6$), 67.60 (C$^5$), 64.00 (CH$_2$O), 57.54 (CH$_3$O), 33.55, 30.29, 24.16, 20.07 (CH$_2$), 14.97 (CH$_3$); $^{19}$F NMR (282 MHz, CDCl$_3$, ref. C$_6$F$_6$) δ: 79.72, 73.61, 47.91, 43.70; m/z (ES$^-$) 719.0 [M]$^-$, 832.9 [M+TFA]$^-$.

$v_{max}$ (film)/cm$^{-1}$ 2932w, 1723m, 1410m, 1192s, 1149s, 1115, 1027s, 922s;

Example 2(iii)

Methyl-4,6-O-benzylidene-3-ethoxymethyl-2-(8-oxa-6,6,7,7,9,9,10,10-octafluoro-decanoic acid-10-sulphonate)-β-D-mannopyranoside amino polystyrene resin amide

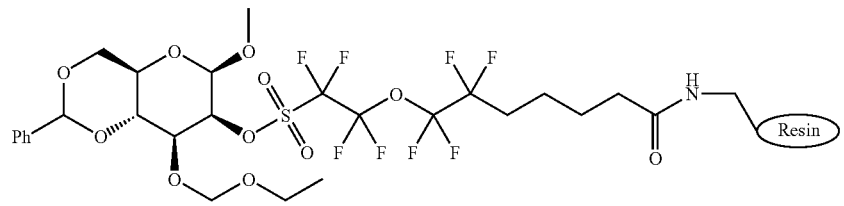

Example 2(ii)

Methyl-4,6-O-benzylidene-3-ethoxymethyl-2-(4-iodo 8-oxa-6,6,7,7,9,9,10,10-Octafluoro-decanoic acid-10-sulphonate)-β-D-mannopyranoside

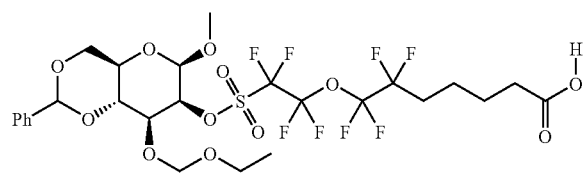

To Methyl-4,6-O-benzylidene-3-ethoxymethyl-2-(4-iodo 8-oxa-6,6,7,7,9,9,10,10-Octafluoro-decanoic acid-10-sulphonate)-β-D-mannopyranoside (prepared as described in Example 2(i)) (300 mg, 0.36 mmol) in Et$_2$O (2 mL) was added zinc (99.998%, 100 mesh, 93 mg, 1.42 mmol) and acetic acid (1 mL) and the reaction refluxed, under argon, for 3 h (bath temp=80° C.). The reaction was allowed to cool to room temperature and filtered through celite, washing with Et$_2$O (50 mL). The filtrate was concentrated in vacuo to remove all of the solvent. Purification by silica gel column To amino-methylated polystyrene (NovaBiochem, 50-100 mesh, 01-64-0383, lot. A24063, loading: 1.5 mmol/g, 45 mg, 0.067 mmol) and Methyl-4,6-O-benzylidene-3-ethoxymethyl-2-(8-oxa-6,6,7,7,9,9,10,10-octafluoro-decanoic acid-10-sulphonate)-β-D-mannopyranoside (prepared as described in Example 2(ii)) (58 mg, 0.081 mmol) in anhydrous CH$_2$Cl$_2$ (1 mL) was added N,N-diisopropylethylamine (21 mg, 28 μL, 0.162 mmol), followed by diphenylphosphoryl chloride (19 mg, 16 μL, 0.081 mmol). The reaction was stirred gently, under argon, at room temperature for 18 h. The resin was removed by filtration, washed with CH$_2$Cl$_2$ (3×10 mL), CH$_3$OH (2×10 mL), Et$_2$O (5×5 mL) and dried in vacuo, at 40° C. for 48 h. This gave methyl-4,6-O-benzylidene-3-ethoxymethyl-2-(8-oxa-6,6,7,7,9,9,10,10-octafluoro-decanoic acid-10-sulphonate)-β-D-mannopyranoside amino polystyrene resin amide as a pale yellow solid (87 mg, 99%).

Loading: theoretical=0.73 mmol/g; found (F microanalysis)=0.55 mmol/g $v_{max}$ (on-bead)/cm$^{-1}$ 2931w, 1662m, 1493m, 1452m, 1410m, 1275m, 1146s, 1094s, 1025s, 919s; $^{19}$F NMR (282 MHz, CDCl$_3$, ref. CFCl$_3$) δ:, −82.01, −88.13, −113.86, −118.23.

Example 3

Preparation of Methyl-4,6-O-benzylidene-3-ethoxymethyl-2-(6-oxa-4,4,5,5,7,7,8,8-Octafluoro-decanoic acid-8-sulphonate)-β-D-mannopyranoside Amino polystyrene Resin amide

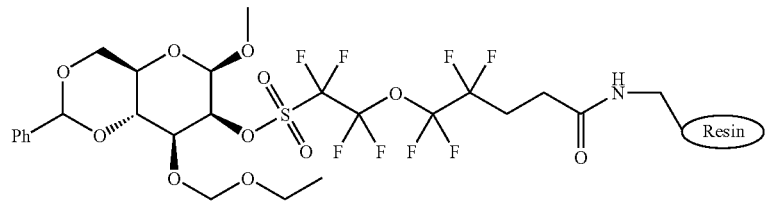

Example 3(i)

Methyl-4,6-O-benzylidene-3-ethoxymethyl-2-(6-oxa-4,4,5,5,7,7,8,8-Octafluoro-decanoic acid-8-sulphonate)-β-D-mannopyranoside

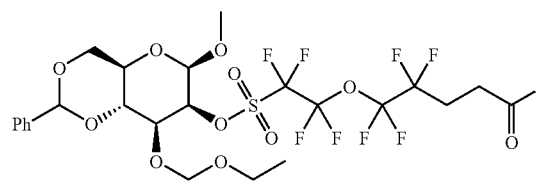

To Methyl-4,6-O-benzylidine-3-ethoxymethyl-2-(5-Iodooctafluoro-3-oxapentane sulphonate)-β-D-mannopyranoside (Intermediate 1), 1.0 g, 1.34 mmol) and acrylic acid (101 mg, 1.41 mmol) in CH$_3$CN:H$_2$O (8 mL:4 mL) was added NaHCO$_3$ (135 mg, 1.61 mmol) and Na$_2$S$_2$O$_4$ (85%, 322 mg, 1.61 mmol) and the reaction stirred at room temperature for 45 mins. The reaction was concentrated in vacuo, dissolved in Et$_2$O (150 mL), washed with water (150 mL) and the aqueous phase re-extracted with Et$_2$O (100 mL). The combined organic phase was washed with brine (150 mL), dried (anhydrous MgSO$_4$) and concentrated in vacuo. Purification by silica gel column chromatography, eluting with EtOAc:hexane (1:4) to EtOAc:hexane (1:0), afforded the desired product as a colourless oil (419 mg, 38%).

$^1$H NMR (300 MHz, CDCl$_3$) δ: 7.52-7.32 (5H, m, Ph), 5.58 (1H, s, PhCHO$_2$), 5.15 (1H, d, J=2.9 Hz, H$^2$), 4.83 (2H, AB, J=7.4 Hz, OCH$_2$O), 4.61 (1H, s, H$^1$), 4.30 (1H, q, J=5.2 Hz, H$^6$), 4.16 (1H, dd, J=2.9, 10.3 Hz, H$^3$), 3.90-3.78 (2H, m, H$^4$, H$^6$), 3.75-3.62 (2H, m, CH$_2$), 3.58 (3H, s, CH$_3$O), 3.51-3.42 (1H, m, H$^5$), 2.68 (2H, t, J=7.4 Hz, CH$_2$), 2.55-2.36 (2H, m, CH$_2$), 1.65-1.15 (3H, t, J=7.4 Hz, CH$_3$);

$^{13}$C NMR (75 MHz, CDCl$_3$) δ: 176.63 (CO), 137.11, 129.31, 128.38, 126.20 (Ph), 101.92 (PhCHO$_2$), 99.19 (C$^1$), 93.93 (OCH$_2$O), 83.61 (C$^2$), 77.23 (C$^4$), 71.09 (C$^3$), 68.41 (C$^6$), 67.58 (C$^5$), 64.01 (CH$_2$O), 57.54 (CH$_3$O), 25.97, 25.69 (CH$_2$), 14.94 (CH$_3$);

$^{19}$F NMR (282 MHz, CDCl$_3$, ref. C$_6$F$_6$) δ: 79.82, 73.56, 47.73, 43.27; m/z (ES$^-$) 804.8 [M+TFA]$^-$, 1382.20 [2M]$^-$.

$v_{max}$ (film)/cm$^{-1}$ 2972w, 1722m, 1412m, 1193s, 1148s, 1096s, 1026s, 921s;

Example 3(ii)

Methyl-4,6-O-benzylidene-3-ethoxymethyl-2-(6-oxa-4,4,5,5,7,7,8,8-Octafluorodecanoic acid-8-sulphonate)-β-D-mannopyranoside Amino Polystyrene Resin amide

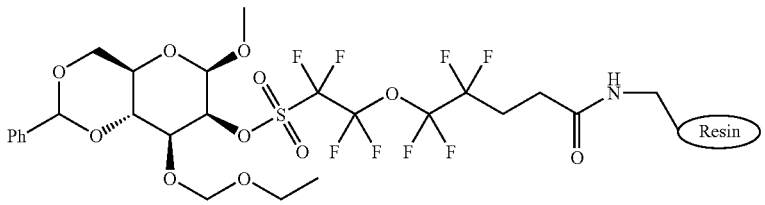

To amino-methylated polystyrene (NovaBiochem, 50-100 mesh, 01-64-0383, lot. A24063, loading: 1.5 mmol/g, 145 mg, 0.218 mmol) and the compound of Example 3(i) (200 mg, 0.289 mmol) in anhydrous CH$_2$Cl$_2$ (2 mL) was added N,N-diisopropylethylamine (75 mg, 100 µL, 0.579 mmol), followed by diphenylphosphoryl chloride (68 mg, 55 µL, 0.289 mmol). The reaction was stirred gently, under argon, at room temperature for 18 h. The resin was removed by filtration, washed with CH$_2$Cl$_2$ (3×5 mL), CH$_3$OH (3×5 mL), Et$_2$O (5×5 mL) dried in vacuo, at 40° C. for 24 h. This gave the title resin as a pale yellow solid (283 mg, 94%).

Loading: theoretical=0.75 mmol/g; found (F microanalysis)=0.80 mmol/g $^{19}$F NMR (282 MHz, CDCl$_3$, ref. CFCl$_3$) δ: −81.84, −87.79, −113.67, −117.96.

Example 4

Preparation of Methyl-4,6-O-benzylidene-3-ethoxymethyl-2-(20-oxa-18,18,19,19,21,21,22,22-Octafluoro-docosanoic acid-22-sulphonate)-β-D-mannopyranoside Amino polystyrene Resin amide

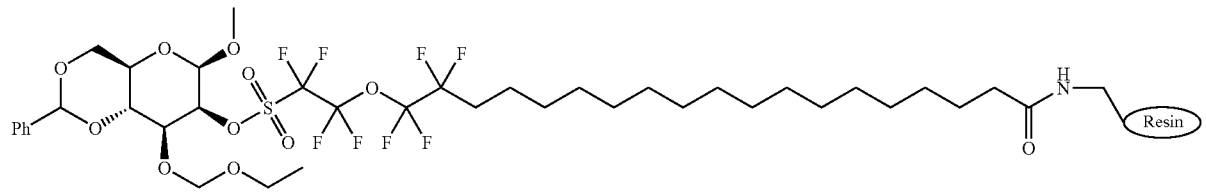

Example 4(i)

Methyl-4,6-O-benzylidene-3-ethoxymethyl-2-(16-iodo-20-oxa-18,18,19,19,21,21,22,22-Octafluoro-docosanoic acid-22-sulphonate)-β-D-mannopyranoside

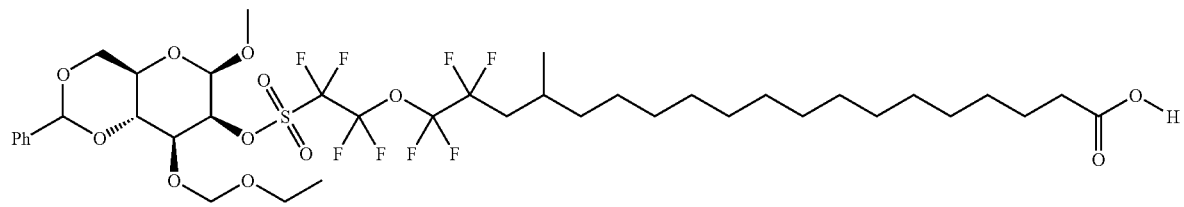

The iodide (Intermediate 1, 1.0 g, 1.34 mmol) and 16-heptadecenoic acid (Apollo Scientific, 378 mg, 1.41 mmol) in $CH_3CN$ (30 mL) formed a cloudy suspension. To this was added $H_2O$ (20 mL) followed by $NaHCO_3$ (135 mg, 1.61 mmol) and $Na_2S_2O_4$ (85%, 322 mg, 16.1 mmol) and the reaction stirred at room temperature for 10 mins. A further portion of MeCN (25 mL) and $H_2O$ (10 mL) was added but the reaction remained cloudy. After 1 h the reaction was concentrated in vacuo, dissolved in $Et_2O$ (100 mL), washed with water (100 mL) and the aqueous phase extracted with $Et_2O$ (50 mL). The combined organic phase was washed with brine (100 mL), dried (anhydrous $MgSO_4$) and concentrated in vacuo to give a crude white cloudy oil. Purification by silica gel column chromatography, eluting with EtOAc:hexane (1:3), afforded Methyl-4,6-O-benzylidene-3-ethoxymethyl-2-(16-iodo-20-oxa-18,18,19,19,21,21,22,22-Octafluoro-docosanoic acid-22-sulphonate)-β-D-mannopyranoside as a colourless oil (230 mg, 17%).

$^1H$ NMR (300 MHz, $CDCl_3$) δ: 7.50-7.31 (5H, m, Ph), 5.58 (1H, s, $PhCHO_2$), 5.15 (1H, d, J=2.9 Hz, $H^2$), 4.85 (2H, AB, J=7.4 Hz, $OCH_2O$), 4.63 (1H, s, $H^1$), 4.40-4.28 (1H, m, CHI, $H^6$), 4.17 (1H, dd, J=2.9, 10.3 Hz, $H^3$), 3.97-3.87 (2H, m, $H^4$, $H^6$), 3.75-3.62 (2H, m, $CH_2$), 3.60 (3H, s, $CH_3O$), 3.52-3.42 (1H, m, $H^5$), 3.00-2.70 (2H, m, $CH_2$), 2.37 (2H, t, J=7.4 Hz, $CH_2$), 1.85-1.40 (4H, m, $CH_2$), 1.30-1.10 (22H, m, $CH_2$), 1.15 (3H, t, J=7.4 Hz, $CH_3$);

$^{13}C$ NMR (100 MHz, $CDCl_3$) δ: 179.04 (CO), 137.56, 129.67, 128.76, 126.62 (Ph), 102.36 ($PhCHO_2$), 99.64 ($C^1$), 94.47 ($OCH_2O$), 84.00 ($C^2$), 77.59 ($C^4$), 71.55 ($C^3$), 68.87 ($C^6$), 68.06 ($C^5$), 64.41 ($CH_2O$), 57.91 ($CH_3O$), 42.02, 41.82, 41.62, 40.91, 34.48, 30.17, 30.14, 30.10, 29.99, 29.93, 29.81, 29.65, 29.10, 25.32 ($CH_2$), 21.79 (CHI), 15.40 ($CH_3$);

$^{19}F$ NMR (282 MHz, $CDCl_3$, ref. $C_6F_6$) δ: 80.20, 73.14, 47.87, 43.76; m/z (ES$^-$) 1013.1 [M]$^-$, 1127.5 [M+TFA]$^-$.

$v_{max}$ (film)/cm$^{-1}$ 2927w, 2855w, 1725m, 1412m, 1194s, 1149s, 1096s, 1026s, 921 s;

Example 4(ii)

Preparation of Methyl-4,6-O-benzylidene-3-ethoxymethyl-2-(20-oxa-18,18,19,19,21,21,22,22-Octafluoro-docosanoic acid-22-sulphonate)-β-D-mannopyranoside To Methyl-4,6-O-benzylidene-3-ethoxymethyl-2-(16-iodo-20-oxa-18,18,19,19,21,21,22,22-Octafluoro-docosanoic acid-22-sulphonate)-β-D-mannopyranoside (prepared as described in Example 4(i)) (200 mg, 0.204 mmol) in Et₂O (4 mL) was added zinc (99.998%, 100 mesh, 80 mg, 1.23 mmol) and acetic acid (2 mL) and the reaction refluxed, under argon, for 3 h (bath temp=80° C.). The reaction was allowed to cool to room temperature and decanted from the zinc, the zinc was washed with Et₂O (3×30 mL). The combined washings were concentrated in vacuo. Purification by silica gel column chromatography, eluting with EtOAc: hexane (1:3), afforded Methyl-4,6-O-benzylidene-3-ethoxymethyl-2-(20-oxa-18,18,19,19,21,21,22,22-Octafluoro-docosanoic acid-22-sulphonate)-β-D-mannopyranoside as a colourless oil (132 mg, 75%).

¹H NMR (300 MHz, CDCl₃) δ: 7.50-7.35 (5H, m, Ph), 5.60 (1H, s, PhCHO₂), 5.15 (1H, d, J=2.9 Hz, H²), 4.83 (2H, AB, J=7.4 Hz, OCH₂O), 4.61 (1H, s, H¹), 4.36 (1H, q, J=5.1 Hz, H⁶), 4.20-4.12 (1H, m, H³), 3.95-3.85 (2H, m, H⁴, H⁶), 3.75-3.60 (2H, m, CH₂), 3.58 (3H, s, CH₃O), 3.51-3.42 (1H, m, H⁵), 2.37 (2H, t, J=7.4 Hz, CH₂), 1.70-1.55 (4H, m, CH₂), 1.40-1.20 (26H, m, CH₂), 1.15 (3H, t, J=7.4 Hz, CH₃);

¹³C NMR (75 MHz, CDCl₃) δ: 179.40 (CO), 137.07, 129.51, 128.60, 126.45 (Ph), 102.19 (PhCHO₂), 99.49 (C¹), 94.28 (OCH₂O), 83.70 (C²), 77.58 (C⁴), 71.43 (C³), 68.71 (C⁶), 67.89 (C⁵), 64.29 (CH₂O), 57.78 (CH₃O), 34.46, 31.02, 30.80, 30.58, 30.04, 29.99, 29.84, 29.80, 29.65, 29.49, 25.17, 21.43, 20.70 (CH₂), 15.21 (CH₃);

¹⁹F NMR (282 MHz, CDCl₃, ref. C₆F₆) δ: 80.01, 74.08, 47.96, 43.34; m/z (ES⁻) 887.1 [M]⁻.

$v_{max}$ (film)/cm⁻¹ 2926w, 2854w, 1711m, 1412m, 1191, 1149s, 1096s, 1027s, 920s;

Example 4(iii)

Methyl-4,6-O-benzylidene-3-ethoxymethyl-2-(20-oxa-18,18,19,19,21,21,22,22-Octafluoro-docosanoic acid-22-sulphonate)-β-D-mannopyranoside Amino polystyrene Resin amide

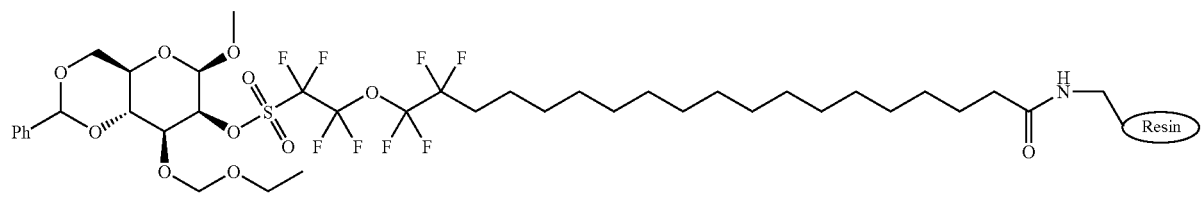

To amino-methylated polystyrene (NovaBiochem, 50-100 mesh, 01-64-0383, lot. A24063, loading: 1.5 mmol/g, 62 mg, 0.093 mmol) and Methyl-4,6-O-benzylidene-3-ethoxymethyl-2-(20-oxa-18,18,19,19,21,21,22,22-Octafluoro-docosanoic acid-22-sulphonate)-β-D-mannopyranoside (prepared as described in Example 4(ii)) (108 mg, 0.121 mmol) in anhydrous CH₂Cl₂ (3 mL) was added N,N-diisopropylethylamine (42 μL, 0.243 mmol), followed by diphenylphosphoryl chloride (29 mg, 0.121 mmol). The reaction was stirred gently, under argon, at room temperature for 18 h. The resin was removed by filtration, washed with CH₂Cl₂ (3×10 mL), CH₃OH (3×10 mL), Et₂O (3×10 mL) and dried in vacuo, 40° C. for 48 h. This gave the Methyl-4,6-O-benzylidene-3-ethoxymethyl-2-(20-oxa-18,18,19,19,21,21,22, 22-Octafluoro-docosanoic acid-22-sulphonate)-β-D-mannopyranoside Amino polystyrene Resin amide as a pale yellow solid (136 mg, 86%).

Loading: theoretical=0.65 mmol/g; found (F microanalysis)=0.52 mmol/g

¹⁹F NMR (282 MHz, CDCl₃, ref. CFCl₃) δ: −82.06, −88.14, −113.93, −118.34.

$v_{max}$(on-bead)/cm⁻¹ 2925m, 1662m, 1493m, 1453m, 1411m, 1146m, 1095s, 1025s;

Comparative Example 5

Preparation of Methyl-4,6-O-benzylidene-3-ethoxymethyl-2-(5-oxa-3,3,4,4,6,6,7,7-Octafluoro-decanoic acid-7-sulphonate)-β-D-mannopyranoside amino polystyrene resin amide

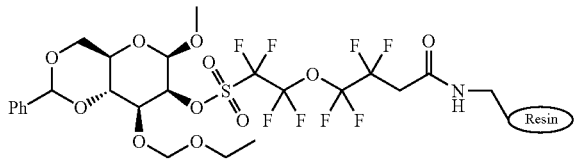

Example 5(i)

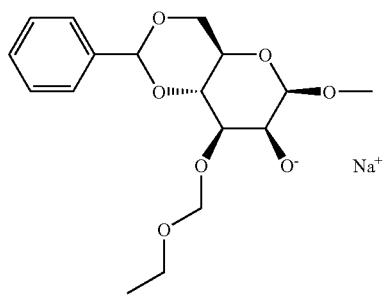

Methyl 4,6-O-benzylidene-3-ethoxymethyl-β-D-mannopyranoside (Intermediate 1(iv)) (0.5 g, 1.47 mmol) was dissolved in THF (10 mL) and NaH (1.1 eq., 1.62 mmol, 0.11 g) was added after washing with dry hexane. The mixture was heated at reflux for 15 minutes under nitrogen to give solution Methyl 4,6-O-benzylidene-3-ethoxymethyl-β-D-mannopyranoside sodium salt in THF.

Example 5(ii)

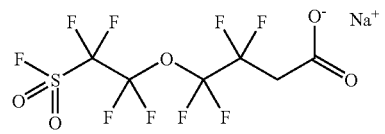

3,3,4,4,6,6,7,7,octafluoro-5-oxo-7-sulphonyl fluoride-heptanoic acid (1.5 eq., 0.79 g, 2.21 mmol) prepared as described in WO 02/055026 was dissolved in THF (10 mL) and NaH (1.1 eq,. 0.162 g, 2.43 mmol) was washed with dry hexane and added to give after stirring for fifteen minutes 3,3,4,4,6,6,7,7,octafluoro-5-oxo-7-sulphonyl fluoride-heptanoic acid sodium salt in THF.

Example 5(iii)

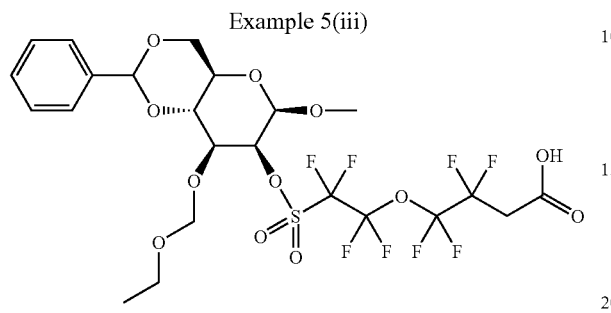

Methyl 4,6-O-benzylidene-3-ethoxymethyl-β-D-mannopyranoside sodium salt in THF (Example 5(i)) was added to 3,3,4,4,6,6,7,7,octafluoro-5-oxo-7-sulphonyl fluoride-heptanoic acid sodium salt in THF. (Example 5(ii)) by pipette and the mixture was stirred at RT for 24 hours under nitrogen. The frosty yellow solution was acidified with 99% acetic acid (6 eq.) and ethyl acetate (50 mL) and water (30 mL) added. The organic layer was separated and the aqueous layer extracted with ethyl acetate. The combined organic washings were dried over $MgSO_4$ and concentrated in vacuo to give a colourless yellow oil which was dried under high vacuum for 3 hours. $^{19}F$ and $^1H$ NMR showed that the reaction gave 60% saturated EOM-mannose-linker in the crude product. This material was purified by reversed phase HPLC on a gilson automated reverse phase system. The fractions were partially evaporated on a rotary evaporator and freeze dried to give Methyl-4,6-O-benzylidene-3-ethoxymethyl-2-(5-oxa-3,3,4,4,6,6,7,7-Octafluoro-decanoic acid-7-sulphonate)-β-D-mannopyranoside as a fluffy white solid (0.3 g, 30%).

$^1$H NMR $CDCl_3$ TMS ref δ: 7.44(2H, benzylidene phenyl), 7.35 (3H, benzylidene phenyl), 5.58 (s, 1H, benzylidene), 5.14 (d, 1H, H-2, J=2.7 Hz), 4.80 (2H, 2 doublets, EOM-$CH_2$, $J^2$=7.5 Hz), 4.60 (s, 1H, H-1), 4.35 (dd, $_1$H, H-3, J=5, 10.5 Hz), 4.12 (dd, 1H, H-4, J=10.5, 10 Hz), 3.89 (2H, 2 quartets, ethyl $CH_2$), 3.70 (2H, two dt's, H-6), 3.56 (s, 3H, 1-OMe), 3.45 (1H, ddd, H-5), 3.08 (t, 2H, $CH_2$—$CF_2$), 1.09 (3H, t, methyl).

$^{19}F$ NMR ($CDCl_3$, $CFCl_3$ reference): δ−82.5, −88.6, −114.3, −117.4.

$C_{23}H_{26}F_8O_{12}S$ requires C, 40.72%; H, 3.86%; F, 22.4%. Found: C, 40.53%; H, 3.94%; F, 21.52.

Example 5(iv)

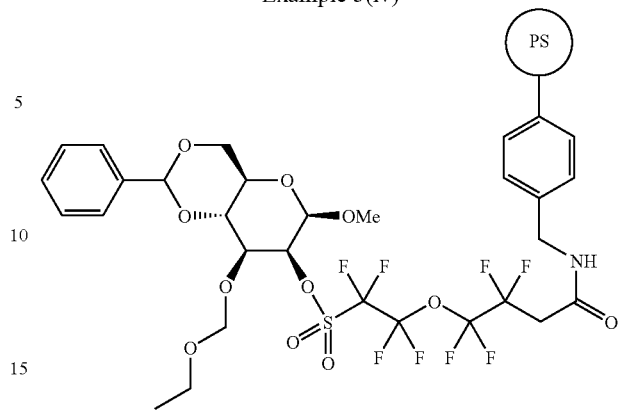

Dlisopropylethylamine (2 mmol, 0.26 g) was added to a solution of Methyl-4,6-O-benzylidene-3-ethoxymethyl-2-(5-oxa-3,3,4,4,6,6,7,7-Octafluoro-decanoic acid-7-sulphonate)-β-D-mannopyranoside Example 5(iii) (0.442 mmol, 0.3 g), aminomethylated PS resin (0.398 mmol, 0.265 g) and diphenylphosphinic chloride (0.885 mmol, 0.21 g) in DCM (8 mL). The mixtures were agitated at RT for 3 hours. The supernatant was filtered off and the resin washed with a Dlisopropylethylamine solution (3×2 mL) (20 mmol in DCM, 36 mL) and DCM then methanol 5 times. The resin was finally dried under vacuum to give Methyl-4,6-O-benzylidene-3-ethoxymethyl-2-(5-oxa-3,3,4,4,6,6,7,7-Octafluoro-decanoic acid-7-sulphonate)-β-D-mannopyranoside amino polystyrene resin amide.

Gel phase $^{19}F$ NMR $CDCl_3$ ref $CFCl_3$: δ −82.4, −89.0, −114.3, −116.0

Elemental Analysis/Loading

| Element | % Found | Calculated Loading mmol/g |
|---|---|---|
| N | 1.25 | 0.89 |
| F | 6.89 | 0.45 |

Example 6

Preparation of Methyl-4,6-O-benzylidene-3-ethoxymethyl-2-(14-oxa-12,12,13,13,15,15,16,16-Octafluoro-hexadecanoic acid-16-sulphonate)-β-D-mannopyranoside Amino methyl phenyl Argopore Resin amide

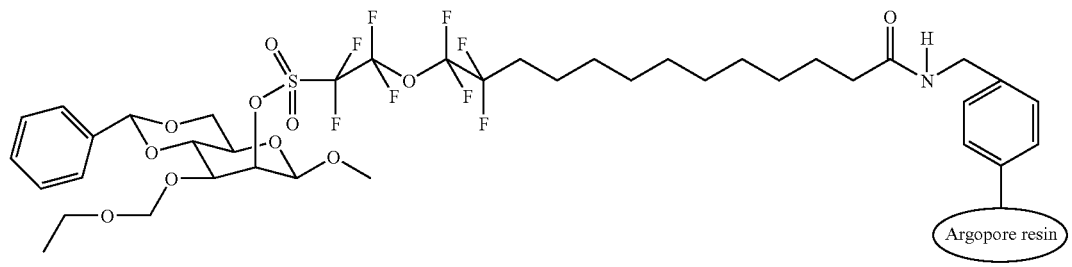

To Argopore (Argonaut Technologies, particle size=134 µm, 800047, lot. 00130, loading: 0.75 mmol/g, 200 mg, 0.15 mmol) and Methyl-4,6-O-benzylidine-3-ethoxymethyl-2-(3-oxa-12,12,13,13,15,15,16,16-Octafluoro-hexadecanoic acid-16-sulphonate)-β-D-mannopyranoside Example 1 (ii) (157 mg, 0.195 mmol) in anhydrous $CH_2Cl_2$ (1.5 ml) was added N,N-diisopropylethylamine (50 mg, 67 µL, 0.39 mmol), followed by diphenylphosphoryl chloride (46 mg, 0.195 mmol). The reaction was stirred gently, under argon, at room temperature for 18 h. The resin was removed by filtration, washed with $CH_2Cl_2$ (3×5 ml), $CH_3OH$ (3×5 ml), $Et_2O$ (5×5 ml) and dried in vacuo, at 40° C. for 24 h. This gave methyl-4,6-O-benzylidene-3-ethoxymethyl-2-(14-oxa-12,12,13,13,15,15,16,16-Octafluoro-hexadecanoic acid-16-sulphonate)-β-D-mannopyranoside Amino methyl phenyl Argopore Resin amide as a pale yellow solid (302 mg, 86% (by weight)).

Loading: theoretical=0.472 mmol/g $v_{max}$ (on-bead)/cm$^{-1}$ 2928m, 1738s, 1493w, 1452m, 1414m, 1373m, 1216s, 1094s, 1026s, 919m;

$^{19}F$ NMR (282 MHz, CDCl$_3$, ref. CFCl$_3$) δ: −82.07, −88.50, −113.65 (broad peaks)

Example 7

Preparation of Methyl-4,6-O-benzylidene-3-ethoxymethyl-2-(14-oxa-12,12,13,13,15,15,16,16-Octafluoro-hexadecanoic acid-16-sulphonate)-β-D-mannopyranoside Amino ethoxy Tenta Gel Resin amide

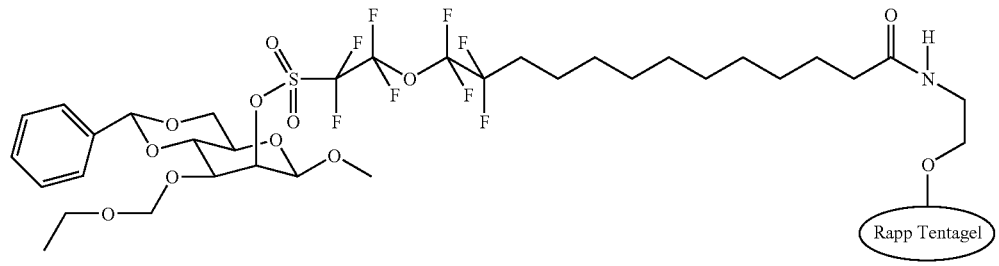

To Tentagel S NH$_2$ (Rapp Polymere, particle size=130 µm, S30 132, loading: 0.25 mmol/g, 200 mg, 0.05 mmol) and Methyl-4,6-O-benzylidine-3-ethoxymethyl-2-(3-oxa-12,12,13,13,15,15,16,16-Octafluoro-hexadecanoic acid-16-sulphonate)-β-D-mannopyranoside Example 1 (ii) (84 mg, 0.104 mmol) in anhydrous $CH_2Cl_2$ (2.5 mL) was added N,N-diisopropylethylamine (26.8 mg, 36 µL, 0.208 mmol), followed by diphenylphosphoryl chloride (24.6 mg, 0.104 mmol). The reaction was stirred gently, under argon, at room temperature for 18 h. The resin was removed by filtration, washed with $CH_2Cl_2$ (3×5 mL), $CH_3OH$ (3×5 mL), $Et_2O$ (5×5 mL) and dried in vacuo, at 40° C. for 24 h. This gave Methyl-4,6-O-benzylidene-3-ethoxymethyl-2-(14-oxa-12,12,13,13,15,15,16,16-Octafluoro-hexadecanoic acid-16-sulphonate)-β-D-mannopyranoside Amino ethoxy Tenta Gel Resin amide as a pale yellow solid (230 mg, 76% (by weight)).

Loading: theoretical=0.21 mmol/g $v_{max}$ (on-bead)/cm$^{-1}$ 3459br, 2914m, 2875m, 1738m, 1453m, 1351m, 1216m, 1091s, 948m;

$^{19}F$ NMR (282 MHz, CDCl$_3$, ref. CFCl$_3$) δ: −82.03, −88.10, −113.92, −118.22.

Example 8

Preparation of Methyl-4,6-O-benzylidene-3-ethoxymethyl-2-(14-oxa-12,12,13,13,15,15,16,16-Octafluoro-hexadecanoic acid-16-sulphonate)-β-D-mannopyranoside Amino ethoxy Argogel Gel Resin amide

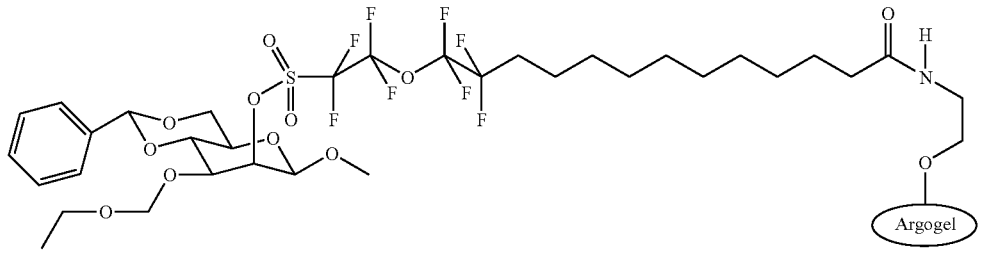

To Argogel (Argonaut Technologies, 800007, loading: 0.40 mmol/g, 200 mg, 0.08 mmol) and the Methyl-4,6-O-benzylidine-3-ethoxymethyl-2-(3-oxa-12,12,13,13,15,15,16,16-Octafluoro-hexadecanoic acid-16-sulphonate)-β-D-mannopyranoside Example 1 (ii) (55 mg, 0.065 mmol) in anhydrous $CH_2Cl_2$ (2.5 ml) was added N,N-diisopropylethylamine 17 mg, 23 µL, 0.13 mmol), followed by diphenylphosphoryl chloride (15.4 mg, 0.065 mmol). The reaction was stirred gently, under argon, at room temperature for 18 h. The resin was removed by filtration, washed with $CH_2Cl_2$ (3×5 ml), $CH_3OH$ (3×5 ml), $Et_2O$ (5×5 ml) and dried in vacuo, at 40° C. for 24 h. This gave Methyl-4,6-O-benzylidene-3-ethoxymethyl-2-(14-oxa-12,12,13,13,15,15,16,16-Octafluoro-hexadecanoic acid-16-sulphonate)-β-D-mannopyranoside Amino alkyl LCAA-CPG Resin amide as a pale yellow solid (244 mg, 70% (by weight)).

Loading: theoretical=0.30 mmol/g $v_{max}$ (on-bead)/cm$^{-1}$ 3483br, 2914m, 2873m, 1738m, 1454m, 1350m, 1216m, 1092s, 948m;

$^{19}F$ NMR (282 MHz, $CDCl_3$, ref. $CFCl_3$) δ: −82.01, −88.08, −113.91, −118.20.

Example 9

Preparation of Methyl-4,6O-benzylidene-3-ethoxymethyl-2-(14-oxa-12,12,13,13,15,15,16,16-Octafluoro-hexadecanoic acid-16-sulphonate)-β-D-mannopyranoside Amino alkyd LCM-CPG Resin amide

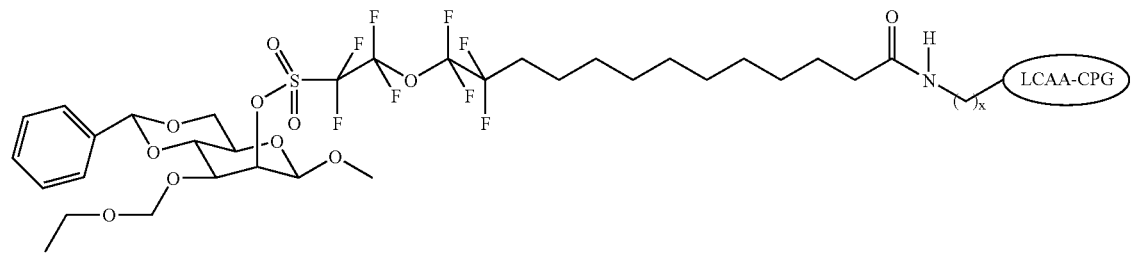

To Long Chain Alkyl Amino Controlled Pore Glass (LCAA-CPG, Link Technologies, loading: 0.092 mmol/g, 200 mg, 0.0184 mmol) and Methyl-4,6-O-benzylidine-3-ethoxymethyl-2-(3-oxa-12,12,13,13,15,15,16,16-Octafluoro-hexadecanoic acid-16-sulphonate)-β-D-mannopyranoside Example 1 (ii)(30 mg, 0.037 mmol) in anhydrous $CH_2Cl_2$ (2 mL) was added N,N-diisopropylethylamine (9.5 mg, 13 µL, 0.074 mmol), followed by diphenylphosphoryl chloride (9 mg, 0.037 mmol). The reaction was rotated gently (not stirred to avoid shattering the glass beads), under argon, at room temperature for 18 h. The resin was removed by filtration, washed with $CH_2Cl_2$ (3×5 mL), $CH_3OH$ (3×5 mL), $Et_2O$ (5×5 mL) and dried in vacuo, at 40° C. for 24 h. This gave Methyl-4,6-O-benzylidene-3-ethoxymethyl-2-14-oxa-12,12,13,13,15,15,16,16-Octafluoro-hexadecanoic acid-16-sulphonate)-β-D-mannopyranoside Amino alkyl LCAA-CPG Resin amide as a white solid (212 mg, 80% (by weight)).

Loading: theoretical=0.086mmol/g

Examples 10-21

Synthesis of resin linker sugar with reduced loadings of the sugar linker by use of less than the stoichiometric amount of sugar linker compared with the amino groups on the resin available for reaction. (Examples 10, 12, 14, 16, 18, 20)

Acetyl capping of unreacted amino groups on resins with less than the stoichiometric loading of sugar linker. (Examples 11, 13, 15, 17, 19, 21)

Loading sugar linker on to the resin in acetonitrile rather than dichloromethane. (Examples 20, 21)

General Procedure for the Synthesis of Examples 10-19

Methyl-4,6-O-benzylidine-3-ethoxymethyl-2-(3-oxa-12,12,13,13,15,15,16,16-octafluoro-hexadecanoic acid-16-sulphonate)-β-D-mannopyranoside prepared as described in Example 1(ii) in dry dichloromethane in a large filter tube was treated with aminopolystryene resin (NovaBiochem 01-64-0143 1.4 mmole/g), diisopropylethylamine (DIPEA) and diphenylphosphinic chloride (DppCl) in that order. The reactions were agitated on a blood wheel at room temperature for 4 h. The reaction liquor was removed by filtration and the resin washed sequentially with dichloromethane and methanol (three times). The resins dried in high vacuum to constant weight to give methyl-4,6-O-benzylidine-3-ethoxymethyl-2-(3-oxa-12,12,13,13,15,15,16,16-octafluoro-hexadecanoic acid-16-sulphonate)-β-D-mannopyranosideamino polystyrene resin amide.

Capping—General procedure Examples 11, 13, 15, 17, 19, 21.

Samples obtained according to Examples 10, 12, 14, 16, 18, and 20 were treated with acetic anhydride and pyridine in DCM in either a reaction tube on a blood wheel (Examples 10, 12, 14, 16, 18) or in a sealed conical flask on a rotary shaker (Example 20) for 2 days. The reaction liquor was removed by filtration and the resins washed sequentially with dichloromethane and methanol (three times). A Kaiser test showed that the resins contained some free primary amine. This was confirmed by colour test with TNBSA. These resins were reacted with acetic anhydride and pyridine once again according to the same procedure for 2 days. The reaction liquor was removed by filtration and the resins washed sequentially with dichloromethane and methanol (three times). The resins were dried in high vacuum to constant weight to give capped Methyl-4,6-O-benzylidine-3-ethoxymethyl-2-(3-oxa-12,12,13,13,15,15,16,16-Octafluoro-hexadecanoic acid-16-sulphonate)-β-D-mannopyranoside amino polystyrene resin amide. A Kaiser test was negative for free amino groups on these resins.

General Procedure for Examples 20-21

As for Examples 10 to 19 but using dry acetonitrile as solvent

Amounts of reagents used in the synthesis of examples 10-21 (table 1)

TABLE 1

| Ex | Loading/ mmol/g | Amount/g | Amount base resin/g | Amount of Linker sugar/g | Dpp-Cl/g | DIPEA/g | $Ac_2O$/g | Py/g | $CH_2Cl_2$/mL |
|----|---|---|---|---|---|---|---|---|---|
| 10 | 0.3   | 0.5 | 0.382 | 0.121  | 0.071 | 0.078 | 0    | 0    | 4    |
| 11 | 0.3   | 0.5 | 0.368 | 0.121  | 0.071 | 0.078 | 0.167| 0.25 | 4    |
| 12 | 0.1   | 1   | 0.921 | 0.080  | 0.047 | 0.057 | 0    | 0    | 10   |
| 13 | 0.1   | 1   | 0.877 | 0.081  | 0.047 | 0.052 | 0.53 | 0.82 | 10   |
| 14 | 0.03  | 3   | 2.929 | 0.0724 | 0.042 | 0.046 | 0    | 0    | 25   |
| 15 | 0.03  | 3   | 2.778 | 0.0724 | 0.042 | 0.046 | 1.80 | 2.79 | 25   |
| 16 | 0.01  | 5   | 4.961 | 0.0402 | 0.023 | 0.026 | 0    | 0    | 50   |
| 17 | 0.01  | 5   | 4.700 | 0.0402 | 0.023 | 0.026 | 3.09 | 4.80 | 50   |
| 18 | 0.003 | 10  | 9.976 | 0.0241 | 0.014 | 0.015 | 0    | 0    | 100  |
| 19 | 0.003 | 10  | 9.50  | 0.0241 | 0.014 | 0.015 | 6.25 | 9.69 | 100  |
| 20 | Max   | 0.3 | 0.148 | 0.155  | 0.09  | 0.1   | 0    | 0    | MeCN |
| 21 | Max   | 0.3 | 0.148 | 0.155  | 0.09  | 0.1   | 0.188| 0.29 | MeCN |

Analytical data collected for examples 10-21

NMR

Gel phase $^{19}F$ NMR samples were prepared as described in example 1(Viii) run in $CDCl_3$ using 128 scans referenced to $CFCl_3$.

Examples 10, 11, 12, 13, 14, 15, 20 and 21 showed 4 peaks at δ=−82.5, −88.5, −114.4, −118.8

The spectra of examples 16 and 17 did not have clearly resolved peaks with 128 scans. No spectrum of examples 18 or 19 was obtained. The signal to noise ratio in the spectra of examples 20 and 21 was in between that of Examples 12 and 14.

Fluorine Elemental analysis

Using the procedures 1 and 2 described in Example 22.

TABLE 2

| Example | % F Proc. 1 | % F Proc. 2 | Average % F | Calculated Loading (mmol/g) |
|---|---|---|---|---|
| 10 | 4.51 | 4.86 | 4.65  | 0.306 |
| 11 | 6.29 | 5.24 | 5.77  | 0.380 |
| 12 | 1.26 | 1.79 | 1.525 | 0.100 |
| 13 | 1.70 | 1.42 | 1.56  | 0.103 |
| 14 | 0.46 | 0.41 | 0.435 | 0.029 |
| 15 | 0.20 | 0.21 | 0.205 | 0.014 |
| 16 | 0.12 | 0.06 | 0.09  | 0.006 |
| 17 | 0.22 | 0.24 | 0.23  | 0.002 |
| 18 | 0.40 | 0.46 | 0.43  | 0.028 |
| 19 | 0.07 | 0.22 | 0.145 | 0.010 |
| 20 | 0.40 | 0.41 | 0.405 | 0.027 |
| 21 | 1.02 | 0.86 | 0.94  | 0.062 |

Example 22

Radiolabelling

Procedure 1 for the Determination of the Yield of FDG on Treatment of a Resin Example with $^{18}F$-Fluoride.

A carbon glass reaction vessel was placed in a brass heater and the pot lid (with three lines attached to allow evaporation, nitrogen flow, and addition of reagents) tightened down and the whole system was leak tested. Kryptofix (22 mg) in acetonitrile (300 ul) and potassium carbonate (8 mg) in water (300 ul), was transferred using a plastic syringe (1 ml) into the carbon glass reaction vessel. The $^{18}F$-fluoride was added and heated to 125° C. At 15 mins three aliquots of acetonitrile (0.5 ml) were added at 1 minute intervals. $^{18}F$-Fluoride was dried up to 40 mins in total. The heater was cooled to room temperature, the pot lid removed and acetonitrile (0.2 ml) was added. The pot lid was replaced and the lines were capped off with stoppers. The heater was set at 100° C. for 10 minutes and the $^{18}F$-fluoride redissolved. After cooling to room temperature once more using a plastic syringe (1 ml), the acetonitrile (0.2 ml) was transferred to a second carbon glass reaction vessel containing the resin (20-25 mg). This carbon glass vessel was transferred to an ion chamber and the labelling activity measured. The carbon glass vessel was replaced in the brass heater and the capped pot lid was tightened down. The reaction was heated to 86° C. for 4 mins before cooling with compressed air. The pot lid was removed acetonitrile (1 ml) was added and the activity in the reaction vessel was measured. Using a plastic syringe (5 ml) and beige needle (19G×2"), the resin was mixed and drawn up in to the plastic syringe (5 ml). The reaction mix was then syringed through a sintered syringe and into a collection vial. The reaction vessel was washed with a further volume of acetonitrile (0.5 ml) and passed through the sintered syringe. The activity in the collection vial and also on the resin and sintered syringe was measured.

Samples were taken for RP HPLC analysis to determine the incorporation yield of $^{18}F$-fluoride into the protected sugar.

Procedure 2 for the Determination of the Yield of FDG on Treatment of a Resin Example with $^{18}F$-Fluoride.

The resin to be tested (30 mgs) is packed into a small teflon cartridge 2 cm×2.5 mm id. This is attached to an HPLC system pre equilibrated with dry MeCN and the flow is established at 50 ul/min. The cartridge is located in an HPLC column heater which is set to raise the cartridge temperature to 85° C.

A mixture of Kryptofix 222, (12.7 mg), aqueous potassium carbonate solution (100 ul), (potassium carbonate (13.4 mg) in water (1 ml)) acetonitrile (0.5 ml) and 37 mmBq of carrier free F-18 fluoride in O-18 water (1 ml) was placed in a drying vessel. The volatile solvents were evaporated by heating at 125° C. under a stream of dry nitrogen for 10 min and the residue allowed to cool, and then redissolved in dry acetonitrile (1 ml). This process was repeated three times to remove any traces of water and the dry residue finally dissolved in 1 ml of acetonitrile.

This solution of F-18 fluoride in acetonitrile (100 ul) was injected onto the cartridge using the HPLC injection valve. A radioactive solution of fluoride consequently flows through the cartridge reacting with resin as it does so. The eluent is monitored using a radiometric and a UV detector. Product exits the column in ~1 cartridge volume within two minutes and the radioactive product is collected and subsequently submitted to reverse phase HPLC analysis and TLC analysis. The ratio of F-18 protected-fluorodeoxyglucose to free 18-fluoride is used to estimate the radiochemical yield. This process also shows if any other chemical species are generated in the reaction.

Results

Radiochemical Yield of Protected FDG as a Function of the Number of $CH_2$'s in the Linker

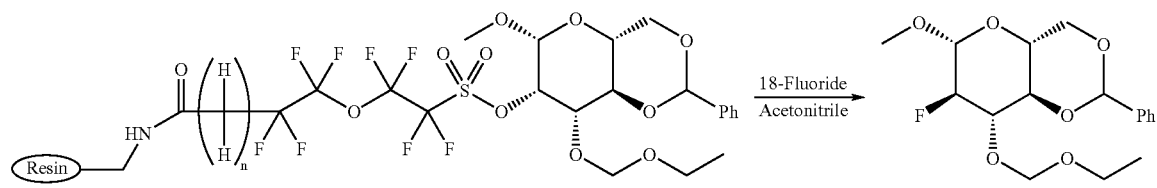

the yield of protected FDG on treatment of Examples (1-5) with fluoride ion is shown in Table 3.

TABLE 3

| Example number | n ($CH_2$'s In linker) | Radiochemical yield % | Fluoride remaining Unreacted % |
|---|---|---|---|
| 5 | 1 | 45-50 | 50-55 |
| 3 | 2 | 75.0 | 25 |
| 2 | 4 | 92.3 | 7.7 |
| 1 | 10 | 85-90 | 10-15 |
| 4 | 16 | 77 | 23 |

Results of the Effect of Loading, Solvent for Loading and Capping on the Radiochemical Yield The yield of protected FDG on treatment of Examples (10-21) with fluoride ion shown that having a sub-maximal loading reduced radiochemical yield, and that where loading is sub-maximal, performing a capping step (as described for Examples 11, 13, 15, 17, 19, and 21) is advantageous.

Example 23

Deprotection Procedure

The solution eluted from the resin was then passed through a silica SepPak cartridge to remove fluoride. The solution collected was placed into a clean carbon glass reaction vessel and the activity was measured in the ion chamber. The carbon glass vessel was then heated to 100° C. for 10 mins to evaporate the solvent, before cooling. HCl (6M, 0.5 ml) was added and heated in a closed system at 120° C. for 5 minutes. After neutralisation with NaOH the reaction mixture was analysed using ion chromatography.

What is claimed is:

1. A compound of formula (I):

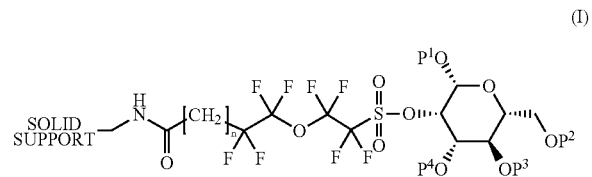

wherein $P^1$, $P^2$, $P^3$, and $P^4$ are each independently hydrogen or a protecting group;
and n is an integer of from 2 to 20.

2. A compound of formula (I) according to claim 1 in which n is 4 to 12.

3. A compound of formula (I) according to claim 1 in which n is 6 to 10.

4. A compound of formula (I) according to claim 1 in which n is 10.

5. A process for the production of 2-$^{18}$F-fluoro-2-deoxy-D-glucose ($^{18}$F-FDG) which comprises treatment of a compound of formula (I) according to claim 1, with $^{18}$F to produce the labelled tracer of formula (II)

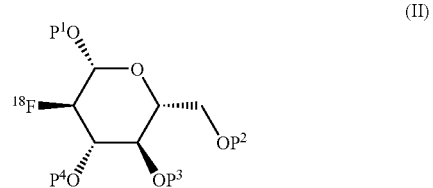

wherein $P^1$, $P^2$, $P^3$, and $P^4$ are each independently hydrogen or a protecting group;
optionally followed by
(i) removal of excess $^{18}F^-$, for example by ion-exchange chromatography; and/or
(ii) removal of the protecting groups; and/or
(iii) removal of organic solvent; and/or
(iv) formulation of the resultant compound of formula (II) as an aqueous solution.

6. A radiopharmaceutical kit for the preparation of $^{18}$F-FDG for use in PET, which comprises:
(i) a vessel containing a compound of formula (I) according to claim 1 and (ii) means for eluting the vessel with a source of $^{18}F^-$;
(iii) an ion-exchange cartridge for removal of excess $^{18}F^-$; and optionally
(iv) a cartridge for solid-phase deprotection of the resultant product of formula (II)

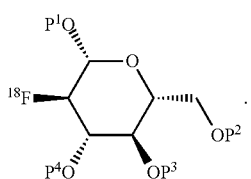
(II)

7. A cartridge for a radiopharmaceutical kit for the preparation of an $^{18}F$-FDG for use in PET which comprises:
(i) a vessel containing a compound of formula (I) according to claim 1; and
(ii) means for eluting the vessel with a source of $^{18}F^-$.

8. A compound of formula (I) according to claim 1 wherein:
n is an integer from 4-12;
$P^1$ is a $C_{1-4}$ alkyl;
$P^4$ is $C_{1-4}$ alkoxymethyl; and
$P^2$ and $P^3$ together with the oxygens to which they are attached form a 1,3-dioxolane.

* * * * *